US008309354B2

(12) United States Patent
Mather et al.

(10) Patent No.: US 8,309,354 B2
(45) Date of Patent: Nov. 13, 2012

(54) HUMAN CANCER STEM CELLS

(75) Inventors: Jennie P. Mather, Millbrae, CA (US); Penelope E. Roberts, Millbrae, CA (US)

(73) Assignee: MacroGenics West, Inc., South San Francisco, CA (US)

(*) Notice: Subject to any disclaimer, the term of this patent is extended or adjusted under 35 U.S.C. 154(b) by 0 days.

(21) Appl. No.: 12/018,126

(22) Filed: Jan. 22, 2008

(65) Prior Publication Data
US 2008/0175870 A1 Jul. 24, 2008

Related U.S. Application Data

(60) Provisional application No. 60/881,497, filed on Jan. 22, 2007, provisional application No. 60/907,180, filed on Mar. 23, 2007, provisional application No. 60/924,247, filed on May 4, 2007, provisional application No. 60/950,714, filed on Jul. 19, 2007, provisional application No. 60/972,613, filed on Sep. 14, 2007.

(51) Int. Cl.
*C12N 5/02* (2006.01)
*C12N 5/00* (2006.01)
*C12N 5/08* (2006.01)
(52) U.S. Cl. ......... 435/378; 435/325; 435/369; 435/371
(58) Field of Classification Search .................. 435/325, 435/369, 371, 378
See application file for complete search history.

(56) References Cited

U.S. PATENT DOCUMENTS

| | | | |
|---|---|---|---|
| 4,816,567 | A | 3/1989 | Cabilly et al. |
| 6,416,999 | B1 | 7/2002 | Li et al. |
| 6,436,704 | B1 | 8/2002 | Roberts et al. |
| 7,148,038 | B2 | 12/2006 | Mather |
| 2005/0106130 | A1 | 5/2005 | Lawman et al. |
| 2005/0136066 | A1 | 6/2005 | Guo |
| 2005/0260208 | A1 | 11/2005 | Eng et al. |

FOREIGN PATENT DOCUMENTS

| | | |
|---|---|---|
| WO | 04001381 A2 | 12/2003 |
| WO | WO 2005/089043 | 9/2005 |
| WO | 2005121179 A2 | 12/2005 |
| WO | WO 2006/030473 | 3/2006 |
| WO | WO 2006/051405 | 5/2006 |
| WO | 2006084075 A2 | 8/2006 |
| WO | 2006084078 A2 | 8/2006 |
| WO | 2006084092 A2 | 8/2006 |
| WO | 2006084226 A2 | 8/2006 |
| WO | 2008091908 A2 | 8/2006 |
| WO | WO 2007/012811 | 2/2007 |
| WO | WO 2007/079293 | 7/2007 |
| WO | WO 2008/039874 | 4/2008 |

OTHER PUBLICATIONS

Soltysova et al., 2005, Neoplasma, vol. 52, No. 6, p. 435-440.*
Kozaki et al., 2000, Cancer Research, vol. 69, p. 2535-2540.*
Fralix et al., 2000, Cancer, vol. 88, No. 9, p. 2010-2021.*
Smith et al., 2001, Molecular Pharmacology, vol. 60, No. 5, p. 885-893.*
Migita et al., 2001, Clinical Cancer Research, vol. 7, p. 2750-2756.*
Jee et al., 2001, Oncogene, vol. 20, p. 198-208.*
Hajj et al., 2003, PNAS, vol. 100, No. 7, p. 3983-3988.*
Allegrucci et al., 2006, Human Reproduction Update, Vol. Advance Access published on Aug. 26, 2006, p. 1-18.*
Sato et al., 2003, Developmental Biology, vol. 260, p. 404-413.*
Rao, M., 2004, Developmental Biology, vol. 275, p. 269-286.*
Abeyta et al., 2004, Human Molecular Genetics, vol. 13, No. 6, p. 601-608.*
Blair et al., 1998, Blood, vol. 92, No. 11, pp. 4325-4335.*
Lapidot et al., 1994, Nature, vol. 367, p. 645-648.*
Singh et al., 2004, Nature, vol. 432, p. 396-401.*
Wang et al., 2005, Trends in Cell Biology, vol. 15, No. 9, p. 494-501.*
PCT International Search Report / Written Opinion WO 2008091908 (Oct. 20, 2008).
Al-Hajj, M et al. (2003) "Prospective identification of Tumorigenic Breast Cancer Cells," Proc. Natl, Acad. Sci. (U.S.A.) 100:3983-3988.
Avigan, D. (1999) "Dendritic Cells: Development, Function and Potential Use for Cancer Immunotherapy," Blood Reviews 13(1):51-64.
Clarke, M.F. et al. (2006) "Stem Cells and Cancer: Two Faces of Eve," Cell 124:1111-1115.
Collins, A.T. et al. (2005) "Prospective Identification of Tumorigenic Prostate Cancer Stem Cells," Cancer Res. 65(23): 10946-19051.
Dick, J.E. (2003) "Breast Cancer Stem Cells Revealed," Proc. Natl. Acad. Sci. (U.S.A.) 100(7):3547-3549.
Hambardzyumyan et al. (2006) "Radiation Resistance and Stem-Like Cells in Brain Tumors p454," Cancer Cell 10 (6):454-456.
Huntley B.J.P. et al. (2005) "Leukemia Stem Cells and the Evolution of Cancer Stem-Cell Research," Nature Rev. 5:311-321.
Li, F. et al. (2007) "Beyond Tumorigenesis: Cancer Stem Cells in Metastasis," Cell Res 17: 3-14.
Lou, H. et al. (2007) "Targeted Therapy For Cancer Stem Cells: The Patched Pathway and ABC Transporters," Oncogene 26:1357-1360.
O'Brien,C.A. et al. (Epub Nov. 19, 2006) "A Human Colon Cancer Cell Capable of Initiating Tumour Growth in Immunodeficient Mice," Nature 445(7123):106-110.
Spisek, R. et al. (2007) "Frequent and specific immunity to the embryonal stem cell-associated antigen SOX2 in patients with monoclonal gammopathy," J. Exp. Med. 204(4):831-40.
Steinman, R.M. (1991) "The dendritic cell system and its role in immunogenicity," Ann. Rev Immunol. 9:271-296.
Timmerman, J.M. et al. (1999) "Dendritic Cell Vaccines for Cancer Immunotherapy," Ann. Rev. Med. 50:507-529.
Woodward, W.A. et al. (Epub Jan. 3, 2007) "WNT/β-Catenin Mediates Radiation Resistance of Mouse Mammary Progenitor Cells," Proc. Natl. Acad. Sci. (U.S.A.) 104(2):618-623.
Singh, S.K. et al. (2003) "Identification of a Cancer Stem Cell in Human Brain Tumors," Cancer Research 63:5821-5828.

(Continued)

*Primary Examiner* — Shin-Lin Chen
(74) *Attorney, Agent, or Firm* — William C. Schrot; Jeffrey I. Auerbach; The Auerbach Law Firm, LLC

(57) ABSTRACT

This invention discloses isolated populations of human cancer stem cells. Methods for characterizing, isolating and culturing human cancer stem cells are also disclosed. Uses for human cancer stem cells are provided.

12 Claims, 6 Drawing Sheets

OTHER PUBLICATIONS

Kozaki, K-i et al. (2001) "Multi-Faceted Analyses of a Highly Metastatic Human Lung Cancer Cell Line NCI-H460-LNM35 Suggest Mimicry of Inflammatory Cells in Metastasis," Oncogene 20:4228-4234.

Hemmati, H.D. et al. (2003) "Cancerous Stem Cells Can Arise from Pediatric Brain Tumors," Proc. Natl. Acad. Sci. (U.S.A.) 100(25):15178-15183.

Singapore Search Report and Written Opinion Prepared by AU Patent Office; SG 200904859-6 (2010) (14 pages).

Ponti, D. et al. (2005) "*Isolation and in vitro Propagation of Tumorigenic Breast Cancer Cells with Stem/Progenitor Cell Properties*," Cancer Res. 65(13):5506-5511.

Todaro, M. et al. (2007) "*Colon Cancer Stem Cells Dictate Tumor Growth and Resist Cell Death by Production of Interleukin-4*," Cell Stem Cell 1: 389-402.

Todaro, M. et al. (2008) "*IL-4-Mediated Drug Resistance in Colon Cancer Stem Cells*" Cell Cycle 7:3:309-313.

Ceder, J.A. et al. (Epub Nov. 21, 2007) "*The Characterization of Epithelial and Stromal Subsets of Candidate Stem/Progenitor Cells in the Human Adult Prostate*," Eur. Urol. 53(3):524-531.

Pellegatta, S. et al. (2006)"*Neurospheres Enriched in Cancer Stem-Like Cells Are Highly Effective in Eliciting a Dendritic Cell-Mediated Immune Response Against Malignant Gliomas*," Cancer Res. 66(21):10247-10252.

European Search Report; EP 08728101.0 (2011) (11 pages).

\* cited by examiner

HUMAN CANCER STEM CELLS

This application claims priority to provisional applications 60/881,497, filed Jan. 22, 2007, 60/907,180, filed Mar. 23, 2007, 60/924,247, filed May 4, 2007, 60/950,714, filed Jul. 19, 2007, 60/972,613, filed Sep. 14, 2007, all of which are incorporated herein by reference in their entireties.

TECHNICAL FIELD

The invention relates generally to human cancer stem cells and methods for their isolation, characterization and use. More specifically, the invention also relates to methods of identifying human cancer stem cells, their uses in therapeutics, target/drug discovery, anti-tumor vaccines and cancer diagnosis and treatment.

BACKGROUND ART

Eliminating cancer from a patient's body is challenging because, although cancerous cells proliferate in an uncontrolled manner, the cells do not necessarily appear to be "foreign" to the body and are therefore difficult to target. Existing cancer treatments tend to be insufficiently targeted to the cancer cells and are destructive to a patient's healthy tissue. Such treatments typically include X-rays, chemotherapy, proton therapy, and surgery. Treatments that incite the body's immune system to exhibit a positive immune response against these cancer cells would be preferred.

Although cancer cells express cancer-associated antigens, they are often able to evade an immune response because of their ability to hide the cancer antigens from the immune system and/or because the exposed antigens are normal, non-mutated differentiation molecules or proteins that the human immune system normally recognizes or tolerates. Cancer stem cells also have been reported that are resistant to current therapies of chemotherapy and radiation. (See, e.g., Targeted therapy for cancer stem cells: the patched pathway and ABC transporters. *Oncogene*, (2007) 26(9):1357-60.; Radiation resistance and stem-like cells in brain tumors. *Cancer Cell* (2006); 10(6):454-6.; WNT/beta-catenin mediates radiation resistance of mouse mammary progenitor cells. *Proc Natl Acad Sci USA* (2007) 104(2):618-23. Epub Jan. 3, 2007)

To effectively use immunotherapy to treat a cancer, a patient must have, or be provided with, a sufficient number of cancer-reactive lymphocytes that can both reach the cancer site and have effector mechanisms to destroy the cancer cells.

Some therapies under investigation are aimed at heightening the immune response in general, and include for example administration of chemical messengers such as cytokines (e.g. IL-2 and/or IL-12), lymphocytes specific for telomerase, bacterial extracts or drugs that boost the immune system. In an attempt to make the immune response more specific for the tumor cells, some treatments administer autologous tumor cells either combined with cytokines—e.g. GM-CSF, gamma interferon or IL-2, individually or in combination—or transfected with the genes that encode these cytokines. Some success has been observed in cell-transfer therapies where autologous lymphocytes are sensitized to cancer cells ex vivo and then infused back into the patient. A similar approach utilizes tumor cell lines instead of autologous tumor cells.

Adjuvants are commonly used with cancer vaccine immunotherapy. One approach uses dendritic cells (DCs) that are highly potent antigen-presenting cells to provoke a positive anti-cancer immune response in patients. Dendritic cells express MHC class I and MHC class II molecules, co-stimulatory molecules and adhesion molecules that provide signals for the stimulation of naive T cells, CD4+ T-helper cells, CD8+ cytotoxic T lymphocytes (CTLs), natural killer (NK) and thymic derived NK cells (NKT) cells. DCs have the capacity to take up various types of molecules. Consequently, DCs can be loaded with tumor-associated antigens (TAAs) in various forms and administered as vaccines.

One DC-based approach uses DC-cancer cell hybrids generated by fusion of cancer cells with dendritic cells to combine sustained cancer antigen expression with the antigen-presenting and immune stimulatory capabilities of the DC. In animal models, immunization with DC-cancer cell hybrids can provide some form of anti-cancer protection or eradicate established disease. Hybrids of autologous DCs comprised of cancer cell lines or primary human cancer cells (including breast carcinoma cells) have been shown to induce CTL responses against autologous cancer cell types in vitro. Clinical studies of the treatment of renal cell carcinoma and glioma have demonstrated that vaccination with DC-cancer cell hybrids can safely induce anti-cancer immune responses in patients.

One hypothesis to explain how tumors grow and metastasize is the cancer stem cell hypothesis, which states that there is a small, distinct subset of cells within each tumor that is capable of indefinite self-renewal and of developing into the more adult tumor cell(s), which are relatively limited in replication capacity. It has been hypothesized that these cancer stem cells (CSC) might be more resistant to chemotherapeutic agents, radiation or other toxic conditions, and thus, persist after clinical therapies and later grow into secondary tumors, metastases or be responsible for relapse. It has been suggested that CSCs can arise either from the tissue stem cells or from a more differentiated tissue progenitor cell(s). While supporting data for this is strong for hematopoietic stem and progenitor cells and hematopoietic tumors, less is known about solid tumors and their respective CSCs.

Solid tumors are thought to arise in organs that contain stem cell populations. The tumors in these tissues consist of heterogeneous populations of cancer cells that differ markedly in their ability to proliferate and form new tumors; this difference in tumor-forming ability has been reported for example with breast cancer cells and with central nervous system tumors. While the majority of the cancer cells have a limited ability to divide, recent literature suggests that a population of cancer cells, termed cancer stem cells, has the exclusive ability to extensively self-renew and form new tumors. Growing evidence suggests that pathways that regulate the self-renewal of normal stem cells are deregulated or altered in cancer stem cells, resulting in the continuous expansion of self-renewing cancer cells and tumor formation.

It has been suggested that cancer patient prognosis is associated with stem cell phenotype/biology. (See e.g., Molecular profiling identifies prognostic subgroups of pediatric glioblastoma and shows increased YB-1 expression in tumors. *J Clin Oncol*. (2007) 25(10):1196-208; Cancer stem cells are central to metastasis, which accounts for 90% of the lethality of cancer. *Cell Res*. (2007) 17:3-14.) It has also been observed that patients with autoimmune reactions to self-stem cells demonstrate decreased cancer progression. (See, e.g. "immunity to cancer stem cells may help protect people with a precancerous condition from developing the full-blown disease" *J Exp Med* (2007) 204(4):831-40.)

Tissue stem cells exist in specific niches or microenvirouments that are critical for maintaining them in the appropriate developmental and metabolic state. These microenvironments are not completely understood, but their disruption by genetically knocking out an important factor can result in the disregulation of stem cell homeostasis both during development and in the adult. In trying to understand the microenvironments that support tissue stem/progenitor cells, many researchers have taken the approach of deriving serum free culture conditions where the medium, substrate and physical environment produce an optimized environment for maintaining specific fetal and neonatal tissue stem/progenitor cells (SPC) in a defined state in which the SPC can replicate, but not differentiate (see for example U.S. Pat. Nos. 6,436,704 and 6,416,999). The optimized media and culture conditions that are distinct for different types of SPC can be seen as recreating the stem cell niche that these cells occupy in vivo. These media and optimized conditions are specifically tailored to the SPCs in that they specifically select out the SPCs and cannot support the survival and/or growth of any other cell types in a tissue. Consequently, non-SPC cells will not survive and replicate under the SPC-preferred conditions and are lost during culture and passage, leaving only a pure SPC population, even when the SPC represents only a very small percentage of the starting culture. The conditions must also remove any signals for further differentiation of the SPC to allow its maintenance in culture over an extended period of time.

One hypothesis about how tumors originate is that tumors arise from the tissue SPC by a series of mutational events. Data exists to suggest that some tumor cells will "home in" to specific SPC niches when they move about the body during the process of metastasis. Media and optimized culture conditions derived to support the survival and growth of SPC might also be able to preferentially support the growth and survival of CSCs, thus selecting for this type of cell when the dispersed tumors are put into culture. Such media and optimized culture conditions may allow for the establishment of pure CSC cultures that would be capable of long-term or extensive growth and maintenance of the characteristics of the rare CSC phenotype.

The tumor stem cell has been hypothesized, but there does not yet exist a reliable way of identifying these cells, nor does consensus exist on all their characteristics. Some researchers have proposed that cancer stem cells can be identified based on marker expression (see e.g., Al-Hajj et al. (2003) *Proc Natl Acad Sci USA* 100:3983-3988; O'Brien et al. (2007) *Nature* 445:106-110; and Clarke et al. (2006) *Cell* 124:1111-5). CD133 has been proposed to be a marker found in cancer stem cells in brain tumors and in human prostatic epithelial stem cells. CD44 expression accompanied by no or low CD24 expression was hypothesized to be expressed by some solid cancer stem cells (e.g., breast cancer). CD34 is a marker present on the surface of blood vessels and immature blood cells that has also been associated with hematopoietic stem cells.

The establishment of pure CSC cultures would be a great advantage in studying and the understanding of the regulation of tumorgenesis and metastasis and in the discovery and development of CSC-directed therapies for cancer. Accordingly, there exists a need for methods to identify, isolate, culture and characterize cancer stem cells.

The invention described herein overcomes many of the unmet needs and shortcomings mentioned above and provides for methods of isolation, maintenance and growth of human cancer stem cells. The invention also describes a constellation of characteristics of cancer stem cells, and specifically the characteristics of a novel population of cells from colon, prostate, lung, pancreas, breast, mantle cell lymphoma, and Merkel's tumors with the biological characteristics of CSCs.

The present invention also provides a simple, effective and efficient method for treating cancer, preventing cancer, delaying the onset of cancer or delaying the progression of cancer via administration of the CSC-based vaccines and treatments described herein.

FIGURES

Figure 3:
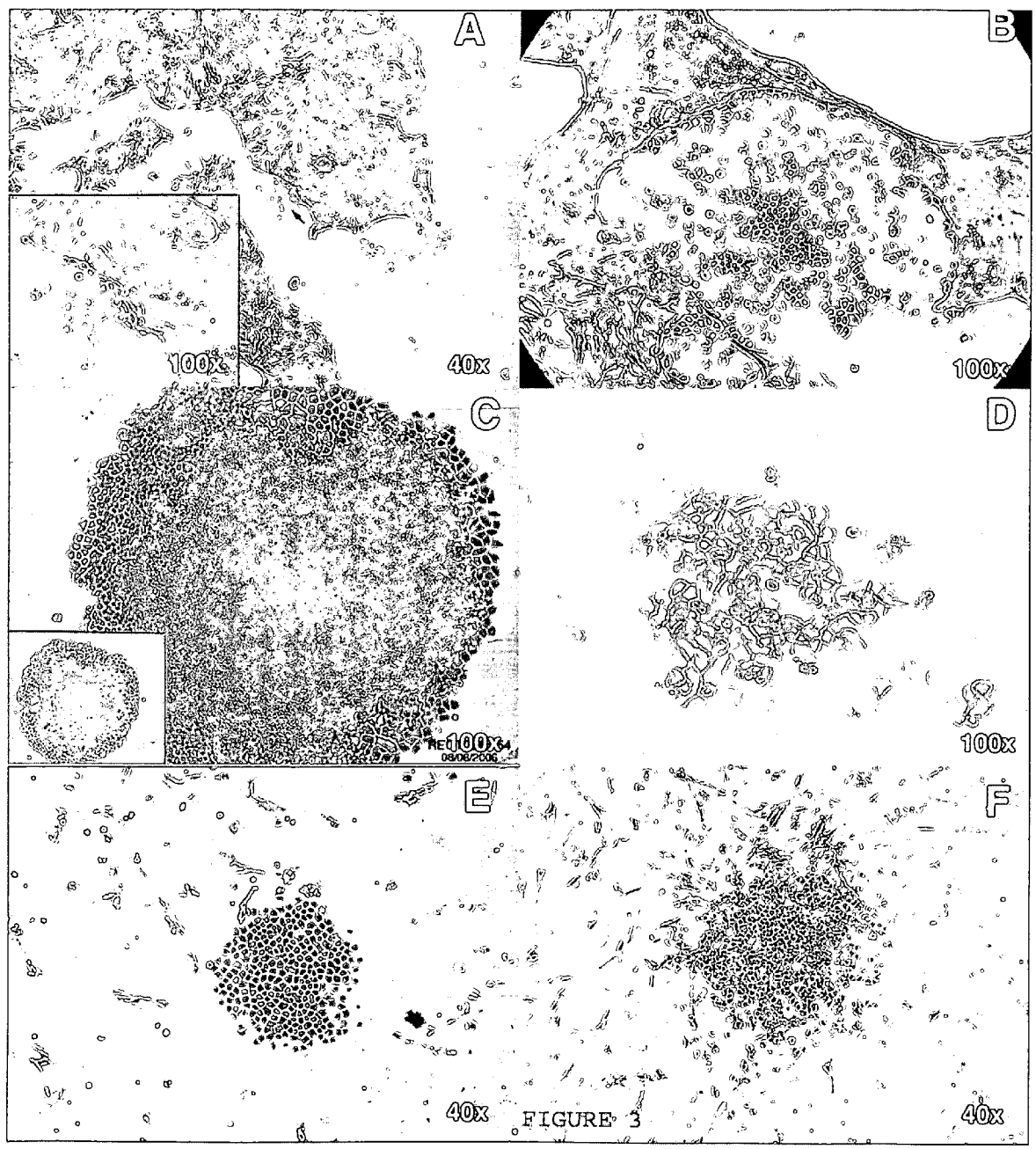

FIG. 3 shows CSC colonies with a similar distinctive morphology growing from colon, (panels A-C, F), Merkel Cell (panel D) and a prostate (panel E) tumor. Panels A and B show cultures derived from a colon tumor: primary culture on day 42 of culture (A) and the same culture area 3 days later (B). Note the small round cells that are apparent in A (arrow and insert) are still dividing, while other cells in the culture die (B). FIG. 3C shows a colon CSC after one passage which has now become almost entirely stem cells. Panels A, B, and D-F show primary cultures where the CSC are beginning to become apparent and the non-stem component of the tumor are either static, dying, or dead. These cultures, with continued passage, have all become CSC lines of this invention as indicated: CRCA1115 (A, B), RECA0515 (C), MCC (D), PRCA0611(E), and CRCA0404 (F).

Figure 4:
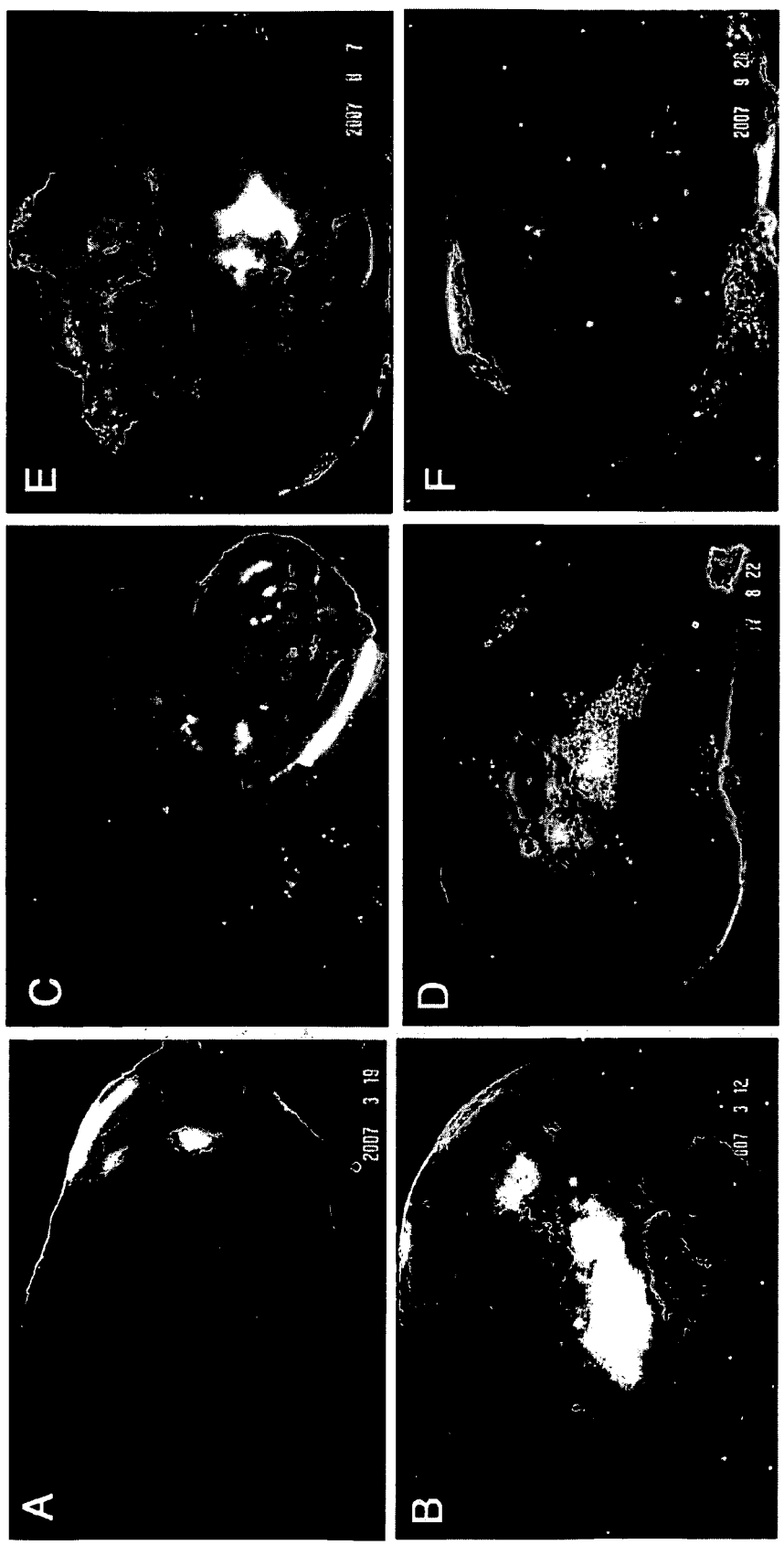
Figure 5:
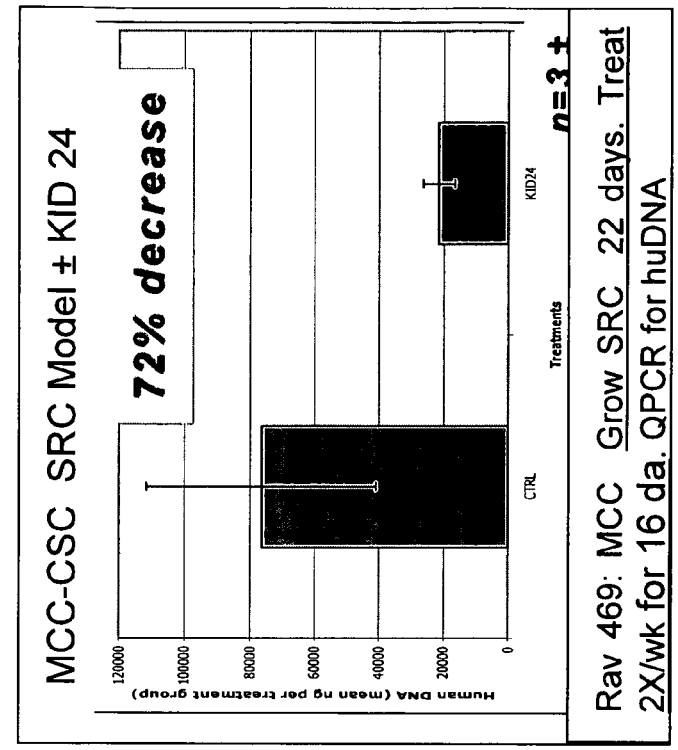
Figure 5:
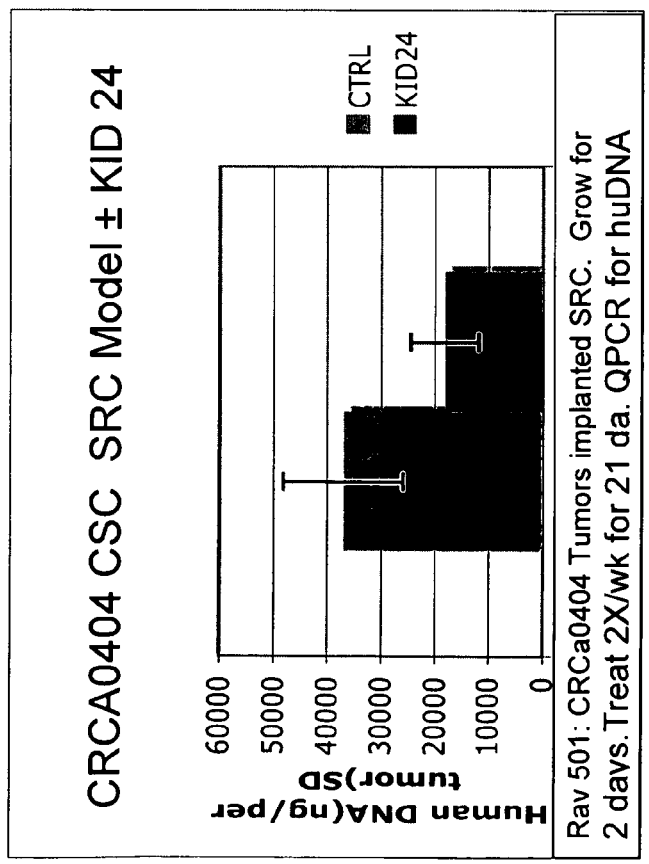

FIG. 4 shows photos of tumors formed under the kidney capsule of SCID mice from various cell lines. On the left are tumors formed from 100 cells each of 2 colon CRC grown for 7 (A-RECA1208) or 8 (B-RECA0515) weeks. Substantial tumors are seen in both cases. The middle panels show the tumor formation from animals implanted with $5 \times 10^4$ cells of CRCA1115 colon CSC (C) after 4.5 weeks or 10 fold ($5 \times 10^5$) more of the non-CSC RECA0705 (D) after 8 weeks. The white fibrous material in D is from the collagen in the implant; the highly refractive material is fat. The human DNA out/in ratio for this tumor is <1.0. The last 2 panels are of kidneys after implantation of $5 \times 10^5$ prostate tumor cells from a CSC. The CSC (E-PRCA0425) cell-derived tumor is shown after 8 weeks. These cells clearly grow more slowly than the colon CSC seen in panel C at 4.5 weeks but do form tumors from 100 cells. Finally panel F is a kidney after implantation of $2.5 \times 10^5$ PRCA0312-43STR cells for 5 weeks. No tumor is visible. Thus the non-CSC lines are clearly distinguished from the CSC lines using this SRC xenograft model FIG. 5 shows that the antibody known as KID24 decreases growth of tumors in cancer stem cell metastatic models established in the subrenal capsule of mice, using the colon (CRCA0404) & Merkel cancer stem cell lines of this invention.

Figure 6:
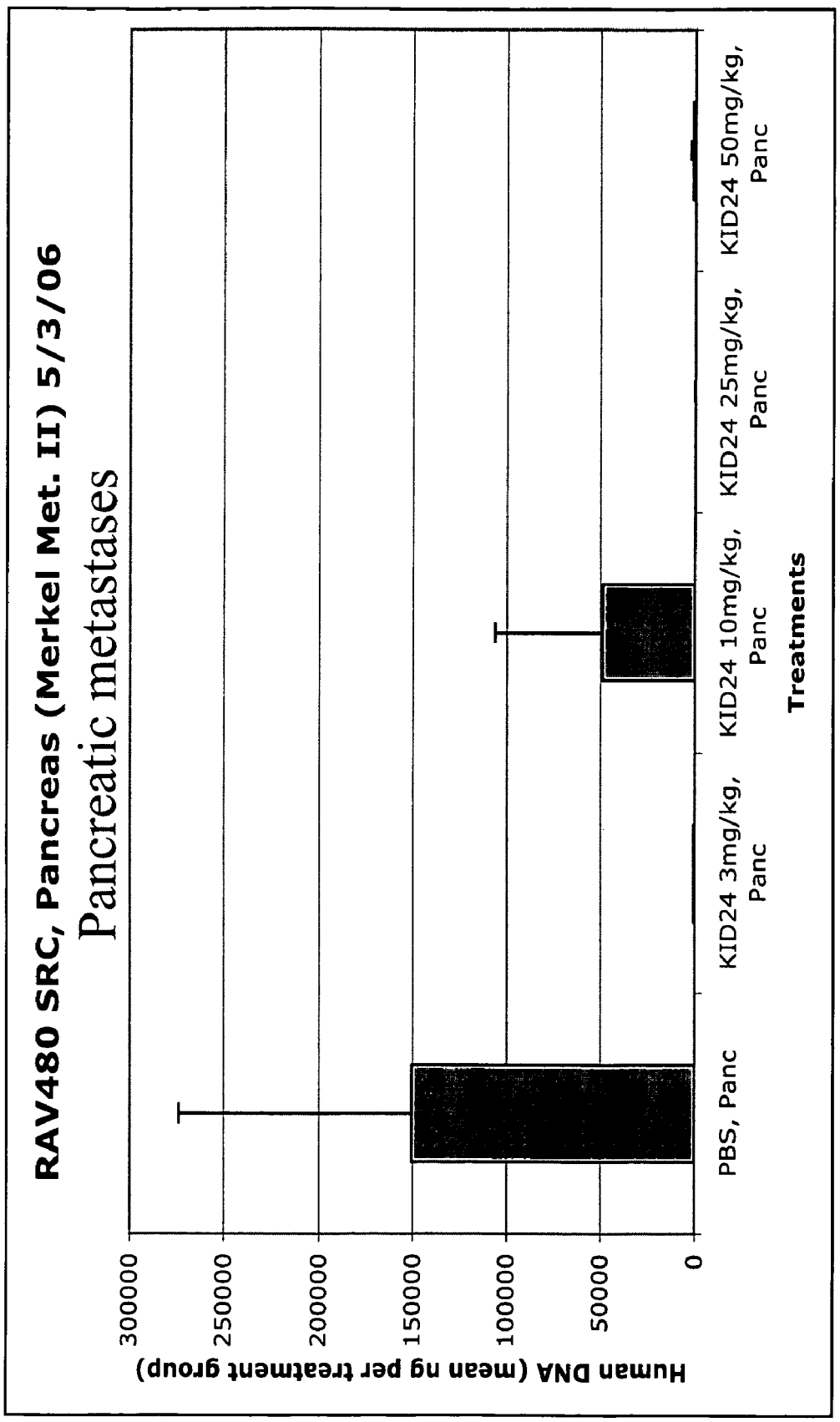

FIG. 6 shows the effect of the antibody known as KID24 on metastases, specifically on Merkel Cell cancer that metastasizes to multiple organs including the pancreas from tumors established in the subrenal capsule. Mets are quantified using the QPCR for huDNA described in the Examples.

DISCLOSURE OF THE INVENTION

This invention relates to the field of tumor biology and cell biology. In one aspect, the invention relates to an isolated population of cancer stem cells cultured from tumor tissue. The cells may be cultured in serum-free nutrient medium, and may have cell surfaces that are substantially free of serum biomolecules. The cells may be maintained in culture without senescence or loss of growth capacity for an extensive period of time.

The cancer stem cells of this invention are useful in drug screening, as tools for genomic and proteomic profiling (in vitro, in vivo and metastatic status) of diseased tissues, for multivalent cancer stem cell vaccines, for diagnostics and imaging of cancer-related antigens, and for the identification of therapeutic agents such as antibodies and drugs.

Another aspect of this invention relates to methods of isolating such a population of substantially pure human cancer stem cells that can be maintained in culture without senescence or loss of growth capacity (ability to self-renew). These methods are based on culturing the human cancer stem cells in an environment that has been optimized for their growth. The nutrient media for culturing human cancer stem cells is based on media formulations that have been optimized for supporting the growth of corresponding fetal progenitor/stem cells.

Another aspect of this invention relates to methods of characterizing such a population of substantially pure human cancer stem cells through functional assays. Such methods are known in the art and are suitable for the characterization of the human cancer stem cells of this invention. Generally such methods are xenograft models for tumor formation in an immune-compromised host animals from the implantation of a small number of human cancer stem cells.

Another aspect of this invention provides methods for characterization of tumor (cancer) stem cell cultures. Such characterization can include the expression of certain markers, including but not limited to CD34, a marker that has been previously associated with hematopoietic stem cells.

In yet another aspect of this invention, this invention relates to methods of generating human tumor xenograft models by introducing a population of human cancer stem cells into a non-human, mammalian recipient.

In another aspect of this invention, the invention relates to methods using a human cancer stem cell or fragment thereof as an immunogen and for suitably providing an isolated cancer stem cell to serve as an immunogen. These methods are useful for the creation of anti-cancer stem cell therapeutic and diagnostic agents, and as vaccine to boost an individual's immune response. The vaccine may be used therapeutically or preventatively. A therapeutic vaccine is administered to a subject having cancer to treat the cancer. In a subject having cancer, the vaccine may be made from the subject's own cancer cells, or from allogenic cancer cells or tumor cell lines. A preventative vaccine is administered to a subject without cancer to reduce the risk of the subject developing cancer.

Another aspect of this invention provides methods of providing a source of human cancer stem cells as biological components for developing pharmaceutical drugs wherein human cancer stem cell cultures are used as a source of cancer stem cell biological components in which one or more of these human cancer stem cell biological components are the targets of the drugs that are being developed.

In another aspect of this invention, the invention relates to methods of providing human cancer stem cell cultures for use in bioassay development. Human cancer stem cell cultures can be used in bioassays to identify factors, agents, or compounds that can affect the growth and/or survival of the human cancer stem cells. Such effects can include the growth promotion, growth arrest, stasis, death, apoptosis, changes in metabolism, changes to gene expression, changes in protein expression or alteration of growth/metabolic pathways. Cancer stem cells can be used in bioassays and/or drug discovery to understand molecular pathways of tumorgenesis, tumor establishment, tumor growth and metastasis.

DETAILED DESCRIPTION OF THE INVENTION

The following detailed description of the invention is provided to aid those skilled in the art in practicing the present invention. This detailed description should not be construed to limit the present invention, as those of ordinary skill in the art may make modifications of the embodiments disclosed herein without departing from the spirit and scope of the present invention. Throughout this disclosure, various publications, patents, and published patent specifications are referenced by citation. The disclosure of these publications, patents, and published patents are hereby incorporated by reference in their entirety into the present disclosure.

The practice of the present invention will employ, unless otherwise indicated, conventional techniques of immunology, molecular biology, microbiology, cell biology and recombinant DNA, which are within the skill of the art. See, e.g., *Molecular Cloning: a laboratory manual*, $2^{nd}$ edition Sambrook, et al. (1989); *Current Protocols In Molecular Biology* F. M. Ausubel, et al. eds., (1987); the series *Methods In Enzymology*, Academic Press, Inc.; *PCR 2: A Practical Approach*, M. J. MacPherson, B. D. Hames and G. R. Taylor, eds. (1995), *Antibodies, A Laboratory Manual*, Harlow and Lane, eds. (1988), *Adult and Pediatric Urology*, J. Gillenwater et al., eds. (2002), and *Animal Cell Culture*, R. I. Freshney, ed. (1987).

As used in the specification and claims, the singular form "a", "an", and "the" include plural references unless the context clearly dictate otherwise. For example, the term "a cell" includes a plurality of cell, including mixtures thereof.

As used in the specification and claims, the terms "cancer stem cell(s)" and "CSC" are interchangeable and refer to solid cancer stem cells. CSCs are mammalian, and in preferred embodiments, these CSC are of human origin, but they are not intended to be limited thereto. As used herein "tumor stem cells" typically refers to cells isolated and cultured from solid human tumors, and are used interchangeably with cancer stem cells.

Cancer stem cells are defined and functionally characterized as a small subset of cells from a tumor that can grow indefinitely in vitro under appropriate conditions (ability for self-renewal), are able to form tumors in vivo using only a small number of cells. Other common approaches to characterize CSCs involve morphology and examination of cell surface markers, transcriptional profile, and drug response.

In embodiments of the present invention, multiple CSC lines have been established from multiple tumor types. These CSCs share some characteristic cell surface antigens and others are distinct. Some embodiments of the CSC lines of this invention can grow indefinitely and form tumors from <20 cells in vivo. Some CSCs are spontaneously metastatic in subrenal capsule animal models or orthotopic xenografts. The CSC lines of this invention and cell lines derived from CSC metastases have characteristic changes in cell surface markers expression, such as CD34 and CD44 expression. Marker expression may change with culture conditions and with cell line passage in an animal.

Cancer stem cell lines described herein have been examined for differential display of cell surface antigens; patterns of cell surface antigen display also differ after passage of cell lines in an animal, in different culture conditions (with or without animal-derived products), and from primary to metastatic tumors, but are stable, over numerous passages in vitro, when the cells are maintained in the preferred media as described. This pattern of cell surface antigen and cell marker changes are useful to identify and characterize the cancer stem cells of this invention.

An "antibody" is an immunoglobulin molecule capable of binding an antigen. As used herein, the term encompasses not only intact immunoglobulin molecules, but also anti-idiotypic antibodies, mutants, fragments, fusion proteins, humanized proteins and modifications of the immunoglobulin molecule that comprise an antigen recognition site of the required specificity.

A "monoclonal antibody" refers to a homogeneous antibody population wherein the monoclonal antibody is comprised of amino acids (naturally occurring and non-naturally occurring) that are involved in the selective binding of an antigen. Monoclonal antibodies are highly specific, being directed against a single antigenic site. The term "monoclonal antibody" encompasses not only intact monoclonal antibodies and full-length monoclonal antibodies, but also fragments thereof (such as Fab, Fab', F(ab')$_2$, Fv), single chain (ScFv), mutants thereof, fusion proteins comprising an antibody portion, humanized monoclonal antibodies, chimeric monoclonal antibodies, and any other modified configuration of the immunoglobulin molecule that comprises an antigen recognition site of the required specificity and the ability to bind to an antigen. It is not intended to be limited as regards to the source of the antibody or the manner in which it is made (e.g., by hybridoma, phage selection, recombinant expression, transgenic animals, etc.).

"Humanized" antibodies refer to a molecule having an antigen-binding site derived from an immunoglobulin from a non-human species and the remaining immunoglobulin structure of the molecule based upon the structure and/or sequence of a human immunoglobulin. The antigen-binding site may comprise either complete variable domains fused onto constant domains or only the complementarity determining regions (CDRs) grafted onto appropriate framework regions in the variable domains.

The term "antigen" is a molecule which can include one or a plurality of antigenic determinants or epitopes to which an antibody can bind. An antigen is a substance that can have immunogenic properties, i.e., induce an immune response. Antigens are considered to be a type of immunogen. As used herein, the term "antigen" is intended to mean full-length proteins as well as peptide fragments thereof containing or comprising one or a plurality of epitopes. Antigens may also comprise one or more antigenic determinant sites, or comprise one or more fragments of such sites, variants of such sites, or peptidomimetics of such sites. Antigens may be protein, partly protein, or non-proteinaceous. These compounds may be glycosylated.

The terms "surface antigens" and "cell surface antigen" are used interchangeably herein and refer to the plasma membrane components of a cell. These components include, but are not limited to, integral and peripheral membrane proteins, glycoproteins, polysaccharides, lipids, and glycosylphosphatidylinositol (GPI)-linked proteins. An "integral membrane protein" is a transmembrane protein that extends across the lipid bilayer of the plasma membrane of a cell. A typical integral membrane protein consists of at least one membrane-spanning segment that generally is comprised of hydrophobic amino acid residues. Peripheral membrane proteins do not extend into the hydrophobic interior of the lipid bilayer and they are bound to the membrane surface by noncovalent interaction with other membrane proteins. GPI-linked proteins are proteins that are held on the cell surface by a lipid tail that is inserted into the lipid bilayer.

"Immunogen" refers to any substance that induces an immune response. A substance that is an immunogen is described as being "immunogenic". Induction of immune response includes but is not limited to activation of humoral responses (e.g., producing antibodies) or cellular responses (e.g., priming cytotoxic T cells), inflammatory responses (e.g., recruitment of leukocytes), and secretion of cytokines and lymphokines.

The term "heterologous" as applied to a cell used for immunization or transplantation means that the cell is derived from a genotypically distinct entity from the recipient. For example, a heterologous cell may be derived from a different species or a different individual from the same species as the recipient. An embryonic cell derived from an individual of one species is heterologous to an adult of the same species. "Heterologous" as applied to a recipient means that the recipient is a genotypically distinct entity from the source of the cells that are being introduced into the recipient.

A cell surface is "substantially free of serum biomolecules" when at least about 50% of the human cancer stem cell surfaces, more preferably at least about 75% of the human cancer stem cell surfaces, even more preferably at least about 90% of the human cancer stem cell surfaces, and most preferably at least about 95% of the human cancer stem cell surfaces do not have serum biomolecules derived from serum binding to the cell surface such that antigenic sites or antibody binding sites are bound or are unavailable for antigenic recognition by an antibody or a portion of an antibody. Cell surface can determined by measuring the cell size, either by microscopy or flow cytometry. For example, synthetic beads of various known sizes are commonly used for calibration in flow cytometry. A small quantity of calibrated beads may be mixed with cancer stem cells and the resultant population is analyzed by flow cytometry. Human cancer stem cells can then be compared with the size of the calibrated beads. Calculations of cell surface amount can be accomplished since the sizes of the beads are known.

"Senescence" as used herein refers to the phenomenon where cells lose the ability to divide.

As used herein, a "substantially pure" population of cells is a population of cells that is comprised at least about 85% of the cells of interest, preferably at least about 90%, and even more preferably about 95% or more.

"Serum," as used herein, refers to the fluid phase of mammalian blood that remains after blood is allowed to clot.

"Serum biomolecules", as used herein, refers to biological compositions found in serum. Examples include, but are not limited to, albumin, a1-globulin, a2-globulin, b-globulin, and g-globulin. Serum biomolecules include biological compositions, whole or partial, which are either naturally found in serum or derived from processing and handling of serum.

The terms "mammals" or "mammalian" refer to warm blooded vertebrates which include but are not limited to humans, mice, rats, rabbits, simians, sport animals, and pets.

Cancer Stem Cell Antigens

In embodiments of the present invention, certain antigens have been detected on the surface of the cancer stem cells disclosed herein. These include known antigens, novel antigens, and antigens not previously associated with tissue or cancer stem cells. By way of example and not of limitation, these antigens include B7H3 (various epitopes), CD46, transferrin receptor, CD112 (polio virus receptor related protein 2), ephA2 receptor, EGFR, ALCAM (CD166), alpha-V-beta-5, JAM3, priopionyl-Coenzyme A carboxylase alpha, carboxypeptidase M, carboxypeptidase C, LDL-receptor, desmoglein2, ADAM9, CEA CD66e, oncostatin M receptor beta, alpha 2 integrin, and prostatin. Cell lines that express these antigens are particularly preferred for use in the methods of these inventions.

Methods for isolating and obtaining these cancer stem cell antigens are common. Preferred methods use antibodies directed against these antigens. Examples of antibodies directed to some of these antigens are provided in the following disclosures: B7H3 (PCT WO 2004/001381 and U.S. 60/733,041, particularly antibody TES7, PTA-7093), CD46

(U.S. Pat. No. 7,148,038, particularly antibody PA7, PTA-3706), transferrin receptor (PCT WO 05/121179, particularly antibody LUCA31, PTA-6055), ephA2 receptor (PCT WO 06/084226, particularly antibody SPL1, PTA-6059), JAM3 (PCT WO 06/084078, particularly antibody PACA4, PTA-6510), carboxypeptidase M (PCT WO 06/076584, particularly antibody KID31, PTA-6516), ADAM9 (PCT WO 06/084075, particularly antibody KID24, PTA-5174), and oncostatin M receptor beta (PCT WO 06/084092, particularly antibody LUCA38, PTA-6511). These antibodies are particularly useful as cancer stem cell markers according to the teachings herein.

These antigens are desirable markers for use in identifying cancer stem cells generally, discovering new cancer stem cells, or for identifying selected subsets of cancer stem cells, such as those that are tissue-specific or developmental-stage specific. The present invention discloses panels of antigens not heretofore appreciated as cancer stem cell specific, thus enabling a means for profiling cells and identifying their stem-cellness. Cells may be selected from a population, using flow analysis and other commonly known means, based on the presence of some or all of the stem cell markers disclosed herein, alone or in combination with other known markers. Routine experimentation is used to determine the presence on a cell surface of the antigens disclosed herein, to permit collection of a unique, cancer stem cell antigen "fingerprint" for a particular tissue, cell or cell culture.

The inventors have identified a set of markers that are present on a predominant number of cancer stem cells from solid tumors. These sets include some or all of the antigens identified above. They are not exclusively present only on cancer stem cells; using the methods taught herein these markers will bind (to some extent) to normal tissue stem cells, normal tissues, tumor tissues, or daughter cells. Many of these antigens are present on both normal and cancer stem cells. Some are present on at least five of the cancer stem cell lines disclosed herein, such as B7H3 (all epitopes). It is expected that the marker profiles of solid tumor-derived cancer stem cells will differ from those derived from hematopoietic cells.

These antigens are also useful for assessing the surface of cells over time. In data not shown, a comparison and differential binding assay was performed using a panel of antibodies and three pairs of cancer stem cell lines: the breast cancer stem cell line BRCA1103 was assessed at passages 11 and 12 to show reproducibility of the assay; rectal carcinoma cancer stem cell line RECA0515 was assessed at passages 10 and 16 to show stability of the cell lines, and colorectal carcinoma cancer stem cell line CRCA0404 was used to compare the parental line and a clone from this line. The antigen profile of the RECA0515 p10 vs p16 was 13% different, the BRCA1103 p11 vs p12 was 2% different, and the CRACA0404 vs clone antigen profile was 6% different.

As disclosed herein, sets of cancer stem cell markers are selected to optimize selection of cells with desired characteristics; for example, the marker profile of daughter cells, cells from metastatic deposits, or cells that have been passaged in vivo will be different from the profile of cancer stem cells from tissues or primary cell culture.

Certain antigens will not be expressed on all cells of a tumor tissue yet will be present on the cancer stem cells from that tumor; methods are commonly known in the field for determining this kind of differential expression.

The methods disclosed herein for use of these cancer stem cell antigens as markers are usefully combined with other methods for identifying cancer stem cells, such as selection using cell culture methods, assessment of phenotype or morphology.

These particularly preferred antigens are desirable vaccine components, presented in a polyvalent vaccine, combination therapeutic composition, or as individual therapeutic compositions for prevention, treatment, or diagnosis of disease. Agents that bind to these cancer stem cell antigens are useful for targeting therapeutic or diagnostic moieties to the cancer stem cells.

Aspects of this invention include isolated cancer stem cells with cancer stem cell morphology that bind to one of more of the antibodies TES7, PA7, LUCA31, SPL1, PACA4, KID31, KID24, and LUCA38.

The cancer stem cells of this invention are also used to discover and screen for antigens that, when bound by ligand, modulate the production of cytokines such as angiogenic and growth factors. For example, the cancer stem cell-binding antibody referred to herein as TES7, directed to an isoform of B7-H3, decreases the secretion of angiogenic factors VEGF and MIP-1 alpha (CCL3) by both stroma cells and cancer stem cells. Both TES7 and the antibody referred to herein as KID24 have been shown to have the ability to modulate cytokine pathways and cytokine signaling. This provides new insight into signaling mechanisms that are capable of driving tumor growth, and cancer stem cells of this invention provide the ability to identify growth modulatory antibodies that would be missed in standard growth assays. According to the teachings of this invention, antibodies raised against antigens present on the cancer stem cells of this invention are used in cytokine assays to determine if the antibody/antigen modulates cytokine signaling. A large variety of cytokine assays suitable for use in the practice of this invention are well known in the art.

Isolation and Maintenance of Solid Cancer Stem Cells.

In preferred embodiments, the human cancer stem cells of this invention are isolated from solid human tumor tissue. The following methods are illustrative rather than limiting; other commonly known methods are acceptable in the practice of this invention.

A solid human tumor tissue is rinsed with phosphate buffered saline (PBS), preferably several times. The PBS may contain antibiotic and/or anti-fungal agents such as, but not limited to gentamycin. The solid human tumor tissue is minced into cubes of approximately 1 mm, suspended in dissociation media. The dissociation media is basal media supplemented with a cell dissociation agent. A wide variety of dissociation agents can be used including but not limited to EDTA, EGTA, trypsin and collagenase-dispase. A preferred dissociation agent is collagenase dispase used at a concentration that will allow for the partial dissociation of cells from the minced tumor tissue. A preferred concentration is 10% weight by volume in PBS. The use of a trypsin inhibitor may also be included in the dissociation media. A preferred trypsin inhibitor is soybean trypsin inhibitor (STI) used at a suitable concentration. As a non-limiting example, one typical suitable concentration of STI is 10%(v/v).

The cells are incubated in the dissociation media at 37° C. At five-minute intervals, the suspension are pipetted to loosen the cell aggregates. The enzymatic activity is stopped when the aggregates are 10-20 cells in size. The cells are pelleted by centrifugation and washed with basal medium and pelleted by centrifugation. The supernatant is removed, the tissue is resuspended in basal medium, then transferred to a culture dish.

A wide variety of basal media are used to keep the pH of the liquid in a range that promotes survival of human solid cancer stem cells. Non-limiting examples include F12/DMEM, Ham's F10 (Sigma), CMRL-1066, Minimal essential medium (MEM, Sigma), RPMI-1640 (Sigma), Dulbecco's Modified Eagle's Medium (DMEM, Sigma), OPTI-MEM® (GIBCO BRL) and Iscove's Modified Eagle's Medium (IMEM). In addition, any of the basal nutrient media described in Ham and Wallace (1979) *Meth. Enz.,* 58:44, Barnes and Sato (1980) *Anal. Biochem.,* 102:255, or Mather, J. P. and Roberts, P. E. (1998) "Introduction to Cell and Tissue Culture", Plenum Press, New York can also be used. In some instances the basal media may use fructose as a sugar source, such as in the media described in patent application publication WO 2005/028626.

Basal medium is added to the culture dish and the tissue is incubated at 37° C. in a humidified atmosphere. In preferred embodiments that promote cancer stem cell survival and growth, a variety of nutrients are added to supplement the basal media, thus creating a "nutrient media". Human cancer stem cell aggregates are placed in this media, and, in a preferred embodiment, the CSCs migrate out of the cell aggregates into the media and anchor to the culture dish or other supplied anchor material. The remnant of the minced tissues that do not attach to the culture dish or anchor will flow in the medium and will be removed by medium change after a short time in culture, e.g., 1-2 weeks.

In another preferred embodiment, cells from human cancer cell aggregates placed in nutrient media all attach to the culture dish and the human cancer stem cells slowly establish and grow amongst the other cell types from the human tumor. Eventually, the human cancer stem cells will form a substantially pure population of cells and the other contaminating cell types will no longer be in the culture. The culture process and environment will not support the replication and/or survival of contaminating cell types and will promote the survival and growth of the human cancer stem cells so as to generate a substantially pure population of human cancer stem cells. The population of human cancer stem cells is capable of long-term growth in culture and is capable of extensive proliferation and growth without senescence.

The human cancer stem cells can be grown in tissue culture containers (e.g., flasks, plates, etc.) that are either uncoated or coated with different substrates. Non-limiting examples of substrates that may be used include fibronectin, laminin, collagen, polylysine, nitrocellulose, nylon, and polytetrafluoroethylene. The size of the tissue culture containers is proportional to the amount of human tumor tissue being placed within the containers. A skilled artisan may determine the correct size of the tissue culture containers by a stepwise increment of tumor tissue placed within the tissue culture containers. When the human tumor tissue is first placed within the tissue culture containers, the media is generally clear in overall turbidity. As cells migrate out and away from the tumor tissue pieces, the media will become more opaque and more turbid. At the point where the media is highly turbid, more nutrient media is placed in the tissue culture containers to replenish the nutrients consumed by the human tumor cells by adding more fresh medium or changing medium completely. Additionally or in the alternative, when the media becomes turbid, a small amount of cells may be removed from the tissue culture containers and checked for cell viability, for example, with trypan blue staining. Tissue culture containers that have been overrun with too many cells will begin to show decreased cell viability.

Continued culture of the human cancer stem cells generally involves transfer of the cells to one or more new culture containers. Preferably, such transfer is done before the culture container is overrun with cells (e.g., as demonstrated by reduced cell viability. The cells may be transferred to other containers of a larger size (e.g., greater cubic volume) to accommodate the increasing amount of cells. Alternately, the cells may by 'split' into several separate tissue culture containers with fresh nutrient media (also known as "subculturing"). In this manner, a substantially pure population of human cancer stem cells can be obtained and propagated.

Removal of cells from a tissue culture container is preferably accomplished by enzymatic treatment to detach the cells from the surface(s) of the plastic tissue culture containers and/or the substrate used (e.g., fibronectin, laminin, etc.). In a more preferred embodiment, an enzyme such as collagenase-dispase is used in an effective amount to dissociate human cancer stem cells from the sides of the tissue culture flask. An effective amount is at least about 10%, more preferably at least about 1%, and most preferably at least about 0.1% collagenase-dispase by volume. After detachment of cells from the surface(s) of the tissue culture container, the enzyme is washed away with a basal media, preferably the nutrient media disclosed herein, and the cells are placed in new culture containers with a nutrient media, preferably the nutrient media disclosed herein. The nutrient media can include growth factors and compounds that are found in the nutrient media optimized for fetal stem/progenitor cells of the same tissue origin as the human cancer stem cells.

The frequency of feeding human cancer stem cells is dependent on the rate of nutrient metabolism of the cells and the stability of the added hormones and growth factors. The higher rate of nutrient metabolism, the more frequent the cells need to be fed. Generally, media acidity will increase as cells metabolize nutrients in the media. Some nutrient media (e.g., RPMI-1640, DMEM, EMEM, etc.) contain pH-sensitive dyes that indicate the acidity such that media changes color when it becomes acidic. Nutrient media can then be added to bring acidity of the existing media to an acidity that will sustain life and promote growth of the cells. Alternatively, a small portion of the cells may be removed from the tissue culture container and assessed for cell viability, for example, with trypan blue staining. If the nutrient media has been metabolized, cell viability will be poor (e.g., less than 50%). A frequency of feeding that is preferable for promoting the survival and growth of human cancer stem cells in serum-free defined medium is about twice a week. The human cancer stem cells of this invention are capable of long-term growth in culture without senescence.

Human Colorectal Carcinoma Stem Cells (CRCA)

Human colorectal carcinoma stem cells are isolated from human colorectal carcinoma tissue. Once the tumor tissue is cleaned, minced and dissociated, it is placed in a colorectal carcinoma stem cell sustaining nutrient media and the CSCs allowed to grow. The nutrient media is a suitable basal media that includes nutrients optimized for the growth and propagation of human colorectal carcinoma stem cells. A preferred embodiment uses F12/DMEM (50:50) basal medium. Examples of supplemental nutrients include, but not limited to insulin, transferrin, epidermal growth factor, selenium, triiodothyronine (T3), ethanolamine, phosphoethanolamine, hydrocortisone, and I-tocopherol (vitamine E). In a preferred embodiment, the following amounts of nutrients are used to promote human colorectal carcinoma stem cell survival and growth: at least about 10 ng/ml insulin and not more than about 1 mg/ml insulin, more preferably about 10 µg/ml insulin; at least about 1 µg/ml transferrin and not more than about 100 µg/ml transferrin, more preferably about 10 µg/ml transferrin; at least about 500 pg/ml epidermal growth factor (EGF) and not more than 5 µg/ml EGF, more preferably 5 ng/ml EGF; at least $1 \times 10^{-10}$ M selenium and not more than $1\times10^{-6}$M selenium, more preferably $2.5\times10^{-8}$M selenium; at least $1\times10^{-14}$M tiiodothyronine (T3) and not more than $1\times10^{-10}$ M T3, more preferably $1\times10^{-12}$M T3; at least $1\times10^{-8}$M ethanolamine and not more $1\times10^{-4}$M ethanolamine, more preferably $1\times10^{-6}$M ethanolamine; at least $1\times10^{-8}$M phosphoethanolamine and not more than $1\times10^{-4}$M phosphoethanolamine, more preferably $1\times10^{-6}$M phosphoethanolamine; at least $1\times10^{-11}$M hydrocortisone and not more than $1\times10^{-7}$M hydrocortisone, more preferably $1\times10^{-9}$M; at least 100 ng/ml vitamin E and not more than 100 μg/ml vitamin E, more preferably 5 μg/ml vitamin E. Antibiotic and/or antifungal agents, such as gentamycin, penicillin, and/or streptomycin may also be added to the medium, but it is preferred that antibiotics/antifungal agents only be added during the initial stages of culture (e.g., the first 2 to 5 days).

The cells can be grown and passaged in a variety of culture vessels that are well known in the art. A preferred embodiment is that the human colorectal carcinoma stem cells are cultured in culture dishes that have been coated with a substrate. There are a variety of culture substrates that are known in the art. Examples of such substrates include, but are not limited to, collagen, fibronectin, laminin, vitronectin, Matrigel and etc. A particularly preferred embodiment is that the human colorectal carcinoma stem cells are grown and passaged on culture dished coated with either fibronectin or laminin.

Human Rectal Carcinoma Stem Cells (RECAs)

Human rectal carcinoma stem cells are isolated from human rectal carcinoma tissue. Once the tumor tissue is cleaned, minced and dissociated, it is placed in a rectal carcinoma stem cell-sustaining nutrient media and the CSCs permitted to grow. The nutrient media is a suitable basal media that includes nutrients optimized for the growth and propagation of human rectal carcinoma stem cells. A preferred embodiment uses F12/DMEM (50:50) basal medium. Examples of supplemental nutrients include, but not limited to insulin, transferrin, EGF, selenium, T3, ethanolamine, phosphoethanolamine, hydrocortisone, vitamin E and porcine pituitary extract (PPE). In a preferred embodiment, the following amounts of nutrients are used to promote human rectal carcinoma stem cell survival and growth: at least about 10 ng/ml insulin and not more than about 1 mg/ml insulin, more preferably about 10 μg/ml insulin; at least about 1 μg/ml transferrin and not more than about 100 μg/ml transferrin, more preferably about 10 μg/ml transferrin; at least about 500 pg/ml epidermal growth factor (EGF) and not more than 5 μg/ml EGF, more preferably 5 ng/ml EGF; at least $1\times10^{-10}$M selenium and not more than $1\times10^{-6}$M selenium, more preferably $2.5\times10^{-8}$M; at least $1\times10^{-4}$M tiiodothyronine (T3) and not more than $1\times10^{-10}$M T3, more preferably $1\times10^{-12}$M T3; at least $1\times10^{-8}$M ethanolamine and not more $1\times10^{-4}$M ethanolamine, more preferably $1\times10^{-6}$M ethanolamine; at least $1\times10^{-8}$M phosphoethanolamine and not more than $1\times10^{-4}$M phosphoethanolamine, more preferably $1\times10^{-6}$M phosphoethanolamine; at least $1\times10^{-11}$M hydrocortisone and not more than $1\times10^{-7}$M hydrocortisone, more preferably $1\times10^{-9}$M; and at least 100 ng/ml vitamin E and not more than 100 μg/ml vitamin E, more preferably 5 μg/ml vitamin E.

Other growth factors may be added to the nutrient media to promote the growth and survival of human rectal carcinoma stem cells. Such growth factors can include, but not be limited to, pituitary extract from animal pituitary. There are many animal pituitary extracts that are known in the art. Examples of preferable pituitary extracts include, but are not limited to human pituitary extract (HPE), bovine pituitary extract (BPE) and porcine pituitary extract (PPE). Preparation of pituitary extracts is well known in the art and can be suitable for the isolation and growth of the human cancer stem cells of this invention.

One preferable method of preparation of porcine pituitary extract includes using 100 grams of porcine pituitaries and adding 250 ml 0.15M NaCl. The pituitary and NaCl mixture is pulsed in a chilled food processor a couple of a times and then pureed in the food processor for approximately 10 or until the desired consistency is achieved. The mixture is then transferred to a beaker and stirred on a magnetic stirrer for approximately 90 minutes. The mixture is then transferred into an appropriate tube and centrifuged for 45 minutes at 18,000 rpm at 4° C. Decant the supernatant and centrifuge the supernatant at 20,000 rpm for 45 minutes at 4° C. Filter the supernatant through a 0.8 μm filter and then through a 0.45 μm filter and finally through a 0.22 μm filter. The concentration of total proteins/ml of PPE can be determined using standard methods known in the art. Preferably, the protein concentration should be approximately 15 mg/ml of PPE. The resulting porcine pituitary extract can be aliquoted and frozen until needed.

Porcine pituitary extract prepared in the above-described method can be added to the nutrient media to promote the survival and growth of the human rectal carcinoma stem cells of this invention. In a preferred embodiment, at least 7 μg total protein of PPE/ml of nutrient media and not more than 7 mg total protein of PPE/ml of nutrient media, more preferably, approximately 75 μg total protein of PPE/ml of nutrient media is added for the survival and growth of the human rectal carcinoma stem cells of this invention.

Antibiotic and/or antifungal agents, such as gentamycin, penicillin, and/or streptomycin may also be added to the medium, but it is preferred that antibiotics/antifungal agents only be added during the initial stages of culture (e.g., the first 2 to 5 days).

The cells can be grown and passaged in a variety of culture vessels that are well known in the art. A preferred embodiment is that the human rectal carcinoma stem cells are cultured in culture dishes that have been coated with a substrate. There are a variety of culture substrates that are known in the art. A particularly preferred embodiment is that the human rectal carcinoma stem cells are grown and passaged on culture dished coated with fibronectin, laminin or a mixture of fibronectin and laminin.

Human Lung Carcinoma Stem Cells

Human lung carcinoma stem cells are isolated from human lung carcinoma tissue. Once the tumor tissue is cleaned, minced and dissociated, the tissue is placed in a lung carcinoma stem cell-sustaining nutrient media and the CSCs are allowed to grow. The nutrient media is a suitable basal media that includes nutrients optimized for the growth and propagation of human lung carcinoma stem cells. A preferred embodiment uses F12/DMEM (50:50) basal medium. Examples of supplemental nutrients include, but not limited to insulin, transferrin, EGF, selenium, and porcine pituitary extract (PPE). In a preferred embodiment, the following amounts of nutrients are used to promote human lung carcinoma stem cell survival and growth: at least about 10 ng/ml insulin and not more than about 1 mg/ml insulin, more preferably about 10 μg/ml insulin; at least about 1 μg/ml transferrin and not more than about 100 μg/ml transferrin, more preferably about 10 μg/ml transferrin; at least about 500 pg/ml epidermal growth factor (EGF) and not more than 5 μg/ml EGF, more preferably 5 ng/ml EGF; at least about $1\times10^{-10}$M selenium and not more than $1\times10^{-6}$M selenium, more preferably $2.5\times10^{-8}$M selenium; and at least 7 μg total protein of PPE/ml and not more than 7 mg total protein of PPE/ml, more preferably 75 μg total protein of PPE/ml. Antibiotic and/or antifungal agents, such as gentamycin, penicillin, and/or streptomycin may also be added to the medium, but it is preferred that antibiotics/antifungal agents only be added during the initial stages of culture (e.g., the first 2 to 5 days).

The cells can be grown and passaged in a variety of culture vessels that are well known in the art. A preferred embodiment is that the human lung carcinoma stem cells are cultured in culture dishes that have been coated with a substrate. There are a variety of culture substrates that are known in the art. Examples of such substrates include, but are not limited to, collagen, fibronectin, laminin, vitronectin, Matrigel and etc. A particularly preferred embodiment is that the human lung carcinoma stem cells are grown and passaged on culture dished coated with fibronectin.

Human Pancreatic Carcinoma Stem Cells

Human pancreatic carcinoma stem cells are isolated from human pancreatic carcinoma tissue. Once the tumor tissue is cleaned, minced and dissociated, it is placed in a pancreatic carcinoma stem cell-sustaining nutrient media and the CSCs are permitted to grow. The nutrient media is a suitable basal media that includes nutrients optimized for the growth and propagation of human pancreatic carcinoma stem cells. A preferred embodiment uses F12/DMEM (50:50) basal medium. Examples of supplemental nutrients include, but not limited to insulin, transferrin, EGF, selenium, T3, ethanolamine, phosphoethanolamine, hydrocortisone, progesterone, forskolin, heregulin and aprotinin. In a preferred embodiment, the following amounts of nutrients are used to promote human pancreatic carcinoma stem cell survival and growth: at least about 10 ng/ml insulin and not more than about 1 mg/ml insulin, more preferably about 10 μg/ml insulin; at least about 1 μg/ml transferrin and not more than about 100 μg/ml transferrin, more preferably about 10 μg/ml transferrin; at least about 500 pg/ml epidermal growth factor (EGF) and not more than 5 μg/ml EGF, more preferably 5 ng/ml EGF; at least $1\times10^{-10}$M selenium and not more than $1\times10^{-6}$M selenium, more preferably $2.5\times10^{-8}$M selenium; at least $1\times10^{-14}$M tiiodothyronine (T3) and not more than $1\times10^{-10}$M T3, more preferably $1\times10^{-12}$M T3; at least $1\times10^{-8}$M ethanolamine and not more $1\times10^{4}$M ethanolamine, more preferably $1\times10^{-6}$M ethanolamine; at least $1\times10^{-8}$M phosphoethanolamine and not more than $1\times10^{-4}$M phosphoethanolamine, more preferably $1\times10^{-6}$M phosphoethanolamine; at least $1\times10^{-11}$M hydrocortisone and not more than $1\times10^{-7}$M hydrocortisone, more preferably $1\times10^{-9}$M; at least $1\times10^{-10}$M progesterone but no more than $1\times10^{-6}$M progesterone, more preferably $1\times10^{-8}$M progesterone; at least 10 nM forskolin but no more than 100 μM forskolin, more preferably about 5 μM forskolin; at least 10 pM heregulin (HRG) but no more than 100 nM heregulin, and more preferably 1-3 nM heregulin; and at least 500 ng/ml aprotinin but no more than 500 μg/ml aprotinin, and more preferably 25 μg/ml aprotinin. Antibiotic and/or antifungal agents, such as gentamycin, penicillin, and/or streptomycin may also be added to the medium, but it is preferred that antibiotics/antifungal agents only be added during the initial stages of culture (e.g., the first 2 to 5 days).

The cells can be grown and passaged in a variety of culture vessels that are well known in the art. A preferred embodiment is that the human pancreatic carcinoma stem cells are cultured in culture dishes that have been coated with a substrate. There are a variety of culture substrates that are known in the art. In a particularly preferred embodiment, the human pancreatic carcinoma stem cells are grown and passaged on culture dishes coated with fibronectin. The human pancreatic carcinoma stem cell cultures can be monitored daily. The culture medium can be collected to supplement the nutrient media of subsequent cultures. In a preferred embodiment, the culture medium of human pancreatic carcinoma stem cells are collected every third day and filtered with a 0.22 μm filter. This conditioned media can be added to subsequent culture at a concentration of at least 1% (vol/vol) but no more than 80% (vol/vol) and more preferably, 20% vol/vol.

Human pancreatic carcinoma stem cells form epithelial-like colonies within 7-10 days of initial plating and these epithelial-like colonies will spread among the non-dividing stromal-like cells. The human pancreatic carcinoma stem can be passaged and sub-cultured. A skilled artisan can determine if the human pancreatic stem cells are ready for sub-culturing. In a preferred embodiment, the human pancreatic carcinoma stem cells can be sub-cultured at least 14 days after the initial plating and no more than 40 days after the initial plating, more preferably 21-24 days after the initial plating. When sub-culturing the human pancreatic carcinoma stem cells, they can be subcultured at least at a 1:2 ratio but no more than a 1:25 ratio and more preferably at a 1:3 ratio onto fibronectin-coated dishes. Aprotinin can be omitted from the culture when no further growth stimulation is observed from the presence of this growth factor.

Human Merkel Cell Carcinoma Stem Cells

Human Merkel cell carcinoma stem cells are isolated from human Merkel cell carcinoma tissue. Once the tumor tissue is cleaned, minced and dissociated, it is placed in a Merkel cell carcinoma stem cell sustaining nutrient media and the CSCs are permitted to grow. The nutrient media is a suitable basal media that includes nutrients optimized for the growth and propagation of human Merkel cell carcinoma stem cells. A preferred embodiment uses F12/DMEM (50:50) basal medium. Examples of supplemental nutrients include, but not limited to insulin, transferrin, EGF, selenium, T3, ethanolamine, phosphoethanolamine, hydrocortisone, forskolin, progesterone and porcine pituitary extract (PPE). Optionally, nerve growth factor β (NGF-β) may be added as a supplemental nutrient to the basal media. In a preferred embodiment, the following amounts of nutrients are used to promote human Merkel carcinoma stem cell survival and growth: at least about 10 ng/ml insulin and not more than about 1 mg/ml insulin, more preferably about 10 μg/ml insulin; at least about 1 μg/ml transferrin and not more than about 100 μg/ml transferrin, more preferably about 10 μg/ml transferrin; at least about 500 pg/ml epidermal growth factor (EGF) and not more than 5 μg/ml EGF, more preferably 5 ng/ml EGF; at least $1\times10^{-10}$M selenium and not more than $1\times10^{-6}$M selenium, more preferably $2.5\times10^{-8}$M selenium; at least $1\times10^{-14}$M tiiodothyronine (T3) and not more than $1\times10^{-10}$M T3, more preferably $1\times10^{-12}$M T3; at least $1\times10^{-8}$M ethanolamine and not more $1\times10^{-4}$M ethanolamine, more preferably $1\times10^{-6}$M ethanolamine; at least $1\times10^{-8}$M phosphoethanolamine and not more than $1\times10^{-4}$M phosphoethanolamine, more preferably $1\times10^{-6}$M phosphoethanolamine; at least $1\times10^{-11}$M hydrocortisone and not more than $1\times10^{-7}$M hydrocortisone, more preferably $5\times10^{-6}$M; at least 10 nM forskolin and not more than 500 μM forskolin, more preferably 1-5 μM forskolin; at least $1\times10^{-10}$M progesterone and not more than $1\times10^{-6}$M progesterone, more preferably $10\times10^{-8}$M progesterone; and at least 7 μg total protein of PPE/ml and not more than 750 μg total protein of PPE/ml, more preferably about 75 μg total protein of PPE/ml. PPE can be omitted from the culture when no further growth stimulation is observed from the presence of this growth factor.

In some cases, nerve growth factor β (NGF-β) may be added to the nutrient media to promote the growth of the Merkel cell carcinoma stem cells. When using NGFβ, use at least 100 pg/ml NGF-β and not more than 1 µg/ml NGF-β, more preferably 10 ng/ml NGF-β. NGF-β can be omitted from the culture when no further growth stimulation is observed from the presence of this growth factor. Antibiotic and/or antifungal agents, such as gentamycin, penicillin, and/or streptomycin may also be added to the medium, but it is preferred that antibiotics/antifungal agents only be added during the initial stages of culture (e.g., the first 2 to 5 days).

The cells can be grown and passaged in a variety of culture vessels that are well known in the art. A preferred embodiment is that the human Merkel cell carcinoma stem cells are cultured in culture dishes that have been coated with a substrate. There are a variety of culture substrates that are known in the art. In a particularly preferred embodiment, the human Merkel cell carcinoma stem cells are grown and passaged on culture dishes coated with fibronectin.

Human Prostate Carcinoma Stem Cells (PRCA)

Human prostate carcinoma stem cells are isolated from human prostate carcinoma tissue. Once the tumor tissue is cleaned, minced and dissociated, it is placed into a prostate carcinoma stem cell sustaining nutrient media and the CSCs are permitted to grow. The nutrient media is a suitable basal media that includes nutrients optimized for the growth and propagation of human prostate carcinoma stem cells. A preferred embodiment uses F12/DMEM (50:50) basal medium with no added calcium. Examples of supplemental nutrients include, but not limited to calcium, insulin, transferrin, EGF, selenium, T3, ethanolamine, phosphoethanolamine, hydrocortisone, testosterone and porcine pituitary extract (PPE).). In a preferred embodiment, the following amounts of nutrients are used to promote human prostate carcinoma stem cell survival and growth: at least about 10 ng/ml insulin and not more than about 1 mg/ml insulin, more preferably about 10 µg/ml insulin; at least about 1 µg/ml transferrin and not more than about 100 µg/ml transferrin, more preferably about 10 µg/ml transferrin; at least about 500 pg/ml epidermal growth factor (EGF) and not more than 5 µg/ml EGF, more preferably 5 ng/ml EGF; at least $1\times10^{-10}$M selenium and not more than $1\times10^{-6}$M selenium, more preferably $2.5\times10^{-8}$M selenium; at least $1\times10^{-14}$M tiiodothyronine (T3) and not more than $1\times10^{-10}$M T3, more preferably $1\times10^{-12}$M T3; at least $1\times10^{-8}$M ethanolamine and not more $1\times10^{-4}$M ethanolamine, more preferably $1\times10^{-6}$M ethanolamine; at least $1\times10^{-8}$M phosphoethanolamine and not more than $1\times10^{-4}$M phosphoethanolamine, more preferably $1\times10^{-6}$M phosphoethanolamine; at least $1\times10^{-11}$M hydrocortisone and not more than $1\times10^{-7}$M hydrocortisone, more preferably $1-5\times10^{-9}$M; at least 50 pg/ml testosterone and not more than 5 µg/ml testosterone, more preferably 50 ng/ml testosterone; and at 150 ng total protein of PPE/ml and not more than 150 µg total protein of PPE/ml, more preferably about 15 µg total protein of PPE/ml. In another preferred embodiment no testosterone is added to the nutrient media. A skilled artisan can determine if the addition of testosterone is advantageous to the growth of the human prostate carcinoma stem cells. Calcium levels can also be varied in the establishment and maintenance of human prostate carcinoma stem cells. In some cases, no added calcium in the nutrient media is advantageous for the establishment of human prostate carcinoma stem cells. In other cases, low levels of added calcium is advantageous for the establishment of human prostate carcinoma stem cells. When using low levels of added calcium in the nutrient media, use at least 1 nM calcium and not more than 100 mM calcium, more preferably 0.1 mM calcium. One skilled in the art would be able to determine if the use of calcium is advantageous for the isolation and/or growth of human prostate carcinoma stem cells.

Antibiotic and/or antifungal agents, such as gentamycin, penicillin, and/or streptomycin may also be added to the medium, but it is preferred that antibiotics/antifungal agents only be added during the initial stages of culture (e.g., the first 2 to 5 days).

The cells can be grown and passaged in a variety of culture vessels that are well known in the art. A preferred embodiment is that the human prostate carcinoma stem cells are cultured in culture dishes that have been coated with a substrate. There are a variety of culture substrates that are known in the art. In a particularly preferred embodiment, the human prostate carcinoma stem cells are grown and passaged on culture dishes coated with laminin.

Human Breast Carcinoma Stem Cells (BRCA)

Human breast carcinoma stem cells are isolated from human breast carcinoma tissue. Once the tumor tissue is cleaned, minced and dissociated, it is placed in a breast carcinoma stem cell sustaining nutrient media. The nutrient media is a suitable basal media that includes nutrients optimized for the growth and propagation of human breast carcinoma stem cells. A preferred embodiment uses F12/DMEM (50:50) basal medium. Examples of supplemental nutrients include, but not limited to insulin, transferrin, EGF, selenium, T3, ethanolamine, phosphoethanolamine, hydrocortisone, prostaglandin E1 and porcine pituitary extract (PPE). In a preferred embodiment, the following amounts of nutrients are used to promote human breast carcinoma stem cell survival and growth: at least about 10 ng/ml insulin and not more than about 1 mg/ml insulin, more preferably about 10 µg/ml insulin; at least about 1 µg/ml transferrin and not more than about 100 µg/ml transferrin, more preferably about 10 µg/ml transferrin; at least about 500 pg/ml epidermal growth factor (EGF) and not more than 5 µg/ml EGF, more preferably 5 ng/ml EGF; at least $1\times10^{-10}$M selenium and not more than $1\times10^{-6}$M selenium, more preferably $2.5\times10^{-8}$M selenium; at least $1\times10^{-4}$M tiiodothyronine (T3) and not more than $1\times10^{-10}$M T3, more preferably $1\times10^{-12}$M T3; at least $1\times10^{-8}$M ethanolamine and not more $1\times10^{-4}$M ethanolamine, more preferably $1\times10^{-6}$M ethanolamine; at least $1\times10^{-8}$M phosphoethanolamine and not more than $1\times10^{-4}$M phosphoethanolamine, more preferably $1\times10^{-6}$M phosphoethanolamine; at least $1\times10^{-10}$M hydrocortisone and not more than $1\times10^{-6}$M hydrocortisone, more preferably $1-5\times10^{-8}$M; at least 10 pg/ml prostaglandin E1 (PGE1) and no more than 100 µg/ml PGE1, more preferably 100 ng/ml PGE1; and at least 150 ng total protein of PPE/ml and more than 150 µg total protein of PPE/ml, more preferably about 15 µg total protein of PPE/ml. Antibiotic and/or antifungal agents, such as gentamycin, penicillin, and/or streptomycin may also be added to the medium, but it is preferred that antibiotics/antifungal agents only be added during the initial stages of culture (e.g., the first 2 to 5 days).

The cells can be grown and passaged in a variety of culture vessels that are well known in the art. A preferred embodiment is that the human breast carcinoma stem cells are cultured in culture dishes that have been coated with a substrate. There are a variety of culture substrates that are known in the art. In a particularly preferred embodiment, the human breast carcinoma stem cells are grown and passaged on culture dishes coated with fibronectin.

After establishing the human breast carcinoma stem cells in culture, the cells may be frozen down using routine methods known in the art. When thawing frozen human breast carcinoma stem cells for culture, it may be advantageous to the establishment of culture to add fetal bovine serum (FBS) during the initial stage of culture (e.g., the first 1 to 5 days). One skilled in the art will be able to determine if the addition of fetal bovine serum during the initial stage of culture after thawing the human breast carcinoma would be advantageous. In a preferred embodiment, 2% FBS (v/v) is added to the nutrient medium during the first stage of culture after thawing the human breast carcinoma stem cells. After 2-5 days, the nutrient medium is changed and the FBS is omitted. Fetal bovine serum is not necessary for the growth of the human breast carcinoma stem cells after the initial thaw.

Human Basal Cell Carcinoma Stem Cells (BCCA)

Human basal cell carcinoma stem cells are isolated from human basal cell carcinoma tissue. Once the tumor tissue is cleaned, minced and dissociated, it is placed in a basal carcinoma stem cell sustaining nutrient media. The nutrient media is a suitable basal media that includes nutrients optimized for the growth and propagation of human basal cell carcinoma stem cells. A preferred embodiment uses F12/DMEM (50:50) basal medium. Examples of supplemental nutrients include, but not limited to insulin, transferrin, EGF, selenium, T3, ethanolamine, phosphoethanolamine, hydrocortisone and porcine pituitary extract (PPE). In a preferred embodiment, the following amounts of nutrients are used to promote human breast carcinoma stem cell survival and growth: at least about 10 ng/ml insulin and not more than about 1 mg/ml insulin, more preferably about 10 µg/ml insulin; at least about 1 µg/ml transferrin and not more than about 100 µg/ml transferrin, more preferably about 10 µg/ml transferrin; at least about 500 pg/ml epidermal growth factor (EGF) and not more than 5 µg/ml EGF, more preferably 5 ng/ml EGF; at least $1\times10^{-10}$M selenium and not more than $1\times10^{-6}$M selenium, more preferably $2.5\times10^{-8}$M selenium; at least $1\times10^{-14}$M tiiodothyronine (T3) and not more than $1\times10^{-10}$M T3, more preferably $1\times10^{-2}$M T3; at least $1\times10^{-8}$M ethanolamine and not more $1\times10^{-4}$M ethanolamine, more preferably $1\times10^{-6}$M ethanolamine; at least $1\times10^{-8}$M phosphoethanolamine and not more than $1\times10^{-4}$M phosphoethanolamine, more preferably $1\times10^{-6}$M phosphoethanolamine; at least $1\times10^{-10}$M hydrocortisone and not more than $1\times10^{-6}$M hydrocortisone, more preferably $1\times10^{-8}$M; and at least 7 µg total protein of PPE/ml and more than 750 µg total protein of PPE/ml, more preferably about 75 µg total protein of PPE/ml.

Antibiotic and/or antifungal agents, such as gentamycin, penicillin, and/or streptomycin may also be added to the medium, but it is preferred that antibiotics/antifungal agents only be added during the initial stages of culture (e.g., the first 2 to 5 days).

The cells can be grown and passaged in a variety of culture vessels that are well known in the art. A preferred embodiment is that the human basal cell carcinoma stem cells are cultured in culture dishes that have been coated with a substrate. There are a variety of culture substrates that are known in the art. In a particularly preferred embodiment, the human breast carcinoma stem cells are grown and passaged on culture dishes coated with fibronectin.

Characterization of Human Cancer Stem Cells

Human cancer stem cells of this invention isolated in the manner disclosed within have several defining characteristics. First, the human cancer stem cells can be characterized by their growth potential (ability to self-renew). The human cancer stem cells are suitable for long-term growth in cell culture without losing their proliferation capacity.

Human cancer stem cells of this invention can be maintained without losing their proliferation capacity in basal nutrient media formulated to be optimized for their growth. The preferred nutrient media disclosed herein may be used to culture the human cancer stem cells in vitro. Different types of substrates or tissue culture plates can be used to enhance the growth of some of the human cancer stem cells.

As is well known to those of ordinary skill in the art, serum is commonly added to nutrient media to further enhance cell growth. Serum and other animal-derived proteins or media additives contain serum biomolecules, and it is particularly preferred that the human cancer stem cells of this invention be grown with none or minimal added serum biomolecules. The serum-free defined medium provided herein is optimized to select for CSCs. The medium provides necessary nutrients and growth factors for growth of the CSCs, while removing any different signal that may be present in serum.

Human cancer stem cells of this invention can be maintained in long-term culture and sub-cultured. At any selected time and after any passage in culture, the human cancer stem cells may be used as an immunogen, for bioassays, to establish human tumor models in xenograft models, or for drug discovery and/or development as disclosed herein.

Characterization of Human Cancer Stem Cells Using Markers

Another characteristic of the human cancer stem cells of this invention is their expression of specific markers. A wide variety of markers have been reported to be expressed in human cancer stem cells, including CD24, CD34, CD133 and CD44. In a preferred embodiment, human cancer stem cells of this invention express CD34. CD34 is a marker that has been reported to be expressed on hematopoietic cancer stem cells. Solid human cancer stem cells in culture have not previously been observed to express CD34. It is a feature of the present invention that the expression of CD34 in solid tumor cells serves as a marker for identification of solid cancer stem cells. The preferred human cancer stem cells of this invention express detectable levels of CD34.

Characterization of Human Cancer Stem Cells by Morphology

Morphological features can identify human cancer stem cells of this invention isolated in the manner disclosed herein. As disclosed herein, human cancer stem cells grow in vitro as either attached cells or in a suspension culture depending on the origin of the tumor from which the human cancer stem cells are isolated. Morphology of human cancer stem cells is small, approximately 8-15 µm in size. When isolating human cancer stem cells in the manner disclosed herein, the human cancer stem cells can be distinguished from the other cell types by their small size. Human cancer stem cells can grow in clusters or islands, eventually forming a monolayer culture. When grown as attached cells, human cancer stem cells can have a cuboidal appearance, although the appearance of the human cancer stem cell can vary depending on the origin of the tumor from which the human cancer stem cells are isolated and the culture conditions. When grown as a suspension culture, human cancer stem cells can be in a rounded and cyst-like cluster and individual cells may have projectile(s).

Functional Characterization of Human Cancer Stem Cells

Another property of human cancer stem cells is their ability to form tumors in vivo from small number of cells in a xenograft. Several xenograft models are suitable for functional characterization of cancer stem cells and are well known in the art. Two preferred xenograft models are subcutaneous implantation of cells in immune-compromised mice and implantation of cells underneath the kidney capsule (or renal capsule) of immune-compromised mice.

When implanting human cancer stem cells in a xenograft model, a substrate can be used for ease of handling the small number of cells. Examples of suitable substrates include, but are not limited to, collagen, laminin, fibronectin, vitronectin, and Matrigel. The human cancer stem cells can be encapsulated in the substrate and the resulting "plug" can be implanted directly into the host animal.

Once implanted into a host animal, the human cancer stem cells are allowed to grow for a suitable amount of time. If a subcutaneous xenograft model is used, the resulting tumor formation can be visually seen in the animal or palpated after a suitable amount of time. If a sub-renal capsule xenograft model is used, the host animal will be sacrificed after a suitable amount of time and the kidney(s) can be visually inspected for the presence of tumor formation. Other methods of detecting tumor formation are also known in the art and can be suitable. For example, quantitative PCR (QPCR) can be performed on the excised kidney(s) using human specific primers. The amount of human DNA can be quantified to determine the extent of tumor formation.

Another method for detecting tumor formation is to excise the tumor and histologically determine if the tumor formed is of human cellular origin. This method is particularly preferred if additional information about the tumor phenotype is important.

Uses of Human Cancer Stem Cells
Immunogen

A use for human cancer stem cells is as an immunogen. As disclosed in this invention, the unique serum-free culturing conditions allow the cell surfaces of the human cancer stem cells to remain free of serum proteins or serum biomolecules that may bind to the surface. Using the disclosed serum-free isolation and culturing techniques avoid a potential problem of antigenic sites that may be "masked" with binding by serum biomolecules. Accordingly, a panel of antibodies may be generated to newly available antigens that were "masked" when using culture conditions containing serum.

Human cancer stem cells isolated and cultured with the methods disclosed herein can be used as an immunogen that is administered to a heterologous recipient. Methods of administrating human cancer stem cells as immunogens to a heterologous recipient include but are not limited to: immunization, administration to a membrane by direct contact such as swabbing or scratch apparatus, administration to mucous membrane by aerosol, and oral administration. As is well known in the art, immunization can be either passive or active immunization. Methods of immunization can occur via different routes that include but are not limited to intraperitoneal injection, intradermal injection, footpad injection, and local injection. The subjects of immunization may include mammals such as mice. The route and schedule of immunization are generally in keeping with established and conventional techniques for antibody stimulation and production. While mice are employed in this embodiment, any mammalian subject including humans or antibody producing cells therefrom can be manipulated according to the processes of this invention to serve as the basis for production of mammalian hybridoma cell lines. Typically, mice are inoculated intraperitoneally with an immunogenic amount of the human cancer stem cells and then boosted with similar amounts of the immunogen. In a preferred embodiment, mice are inoculated via footpad injection with an immunogenic amount of the human cancer stem cells, with or without adjuvant, and then boosted with similar amounts of the immunogen. In an alternative, cells grown on non-biological membrane matrix, are surgically implanted intraperitoneally into the host mammal. Lymphoid cells, preferably spleen lymphoid cells from the mice, are collected a few days after the final boost and a cell suspension is prepared therefrom for use in the fusion.

Hybridomas are prepared from the lymphocytes and immortalized myeloma cells using the general somatic cell hybridization technique of Kohler, B. and Milstein, C. (1975) *Nature* 256:495-497 as modified by Buck, D. W., et al., (1982) *In Vitro*, 18:377-381. Available myeloma lines, including but not limited to X63-Ag8.653 and those from the Salk Institute, Cell Distribution Center, San Diego, Calif., USA, may be used in the hybridization. The technique involves fusing the myeloma cells and lymphoid cells using a fusogen such as polyethylene glycol, or by electrical means well known to those skilled in the art. After the fusion, the cells are separated from the fusion medium and grown in a selective growth medium, such as HAT medium, to eliminate unhybridized parent cells. Any of the media described herein can be used for culturing hybridomas that secrete monoclonal antibodies. As another alternative to the cell fusion technique, EBV immortalized B cells are used to produce the monoclonal antibodies of the subject invention. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that produce such antibodies may be grown in vitro or in vivo using known procedures. The monoclonal antibodies may be isolated from the culture media or body fluids by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen.

Monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. Prokaryotic hosts, such as *E. coli* are also suitable for the recombinant production of antibodies herein. The DNA also may be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide. Such a non-immunoglobulin polypeptide can be substituted for the constant domains of an antibody produced from using the cells of the invention as an immunogen, or can be substituted for the variable domains of one antigen-combining site of an antibody produced from using the cells of the invention to create a chimeric bivalent antibody.

In this manner, a panel of novel antibodies to cell surface antigen specific to human cancer stem cells can be generated using the human cancer stem cells of this invention. Once monoclonal antibodies to cell surface antigens on human cancer stem cells are made by the method disclosed herein, the antibodies have several uses.

The antibodies may be sequenced and cloned for purposes of generating recombinant antibodies or humanized antibodies. Other uses of human cancer stem cell-specific antibodies include, but are not limited to, biological testing and purification (e.g., isolating human cancer stem cells by flow cytometry or panning), therapeutic uses (e.g., promoting or arresting cell growth by binding of antibody to target cell or promoting or arresting growth of a cell mass by binding of antibody to target cell), biological markers (e.g., identification of other human cancer stem cells), and clinical diagnosis (e.g., identification of human cancer stem cells).

Vaccines

The present invention contemplates the disclosed cancer cell vaccines for use in both active and passive immunization. Immunogenic compositions, useful as vaccines, may be prepared most readily from immunogenic peptides and a select cancer cell. The cancer cell will be from host cancer cells or from the same type of cancer cells, which may be obtained from appropriate cell lines or from non-autologous tumor cells.

The subject tumor cells are useful for generating cellular vaccines. A variety of methods for generating cellular vaccines known in the art are applicable (see, e.g., US Application Nos. 20050136066, 20050106130, and 20050260208). In particular, one type of antigen presenting cell, dendritic cells, has recently become of interest in the area of cancer immunotherapy. Dendritic cells are bone marrow-derived cells that can internalize antigen and process the antigen such that it is presented in the context of both the MHC class I complex and the MHC class II complex. In some aspects, a dendritic cell used in the subject invention is able to activate both CD8+ T cells (which are primarily cytotoxic T lymphocytes) and CD4+ T cells (which are primarily helper T cells). It should be understood that any cell capable of presenting a peptide derived from an internalized antigen on both class I and class II MHC is a dendritic cell of the invention (Steinman, *Annu. Rev. Immunol.* 9: 271-296 (1991)). In this capacity, dendritic cells can be used to present an antigen of interest to T cells. Several approaches have been adopted to directly load tumor antigens onto dendritic cells, including the pulsing of tumor peptides onto mature dendritic cells (Avigan, Blood Reviews 13: 51-64 (1999)). Isolated dendritic cells loaded with tumor antigen ex vivo and administered as a cellular vaccine have been found to induce protective and therapeutic anti-tumor immunity in experimental animals (Timmerman et al., Annu. Rev. Med. 50:507-529 (1999).

In one aspect, a CSC is allowed to contact in vivo or ex vivo an antigen presenting cell, such as a dendritic cell. Upon uptake of the antigens of the CSC by the dendritic cell, cellular vaccines are expected to be generated by other lymphocytic cells to which the antigen is presented. In addition to dendritic cells, other cells useful for presenting agents include but are not limited to macrophages, B cells, and other cells fused with a CSC of the present invention.

In other embodiments, the therapeutic composition used for vaccination or with the other methods of this invention is not an intact CSC, instead it is a purified cell membrane preparation that serves as a vaccine to induce or augment the endogenous response to the tumor in a subject. The immunogen in these embodiments consists of plasma membrane fragments or vesicles, preferably oriented right side out and administered to a patient in such a way as to induce an immune response in a patient with cancer to epitopes shared between the cells that are the source of the immunogen and the patient's own cancer cells.

The cells originating the plasma membrane vesicles (PMV) comprise CSCs of the present invention that expresses a variety of oncofetal antigens commonly expressed by tumors of the originating type. Alternatively they could be fetal tissue stem cells, not cancer stem cells.

The cancer cell vaccines will typically be prepared as injectables, in the form of suspensions. The cell suspensions may be mixed with excipients that are pharmaceutically acceptable and compatible with the cells. Suitable excipients include, for example, water, saline, dextrose, glycerol, ethanol or the like and combinations thereof. In addition, if desired, the vaccine may contain minor amounts of auxiliary substances such as wetting or emulsifying agents, pH buffering agents, or adjuvants that enhance the effectiveness of the vaccine.

Vaccines are conventionally administered parenterally, by injection, for example, either subcutaneously or intramuscularly and are administered in a manner compatible with the dosage formulation, and in such amount as will be therapeutically effective and immunogenic. Alternatively, intradermal injection of the vaccine may be preferable. The quantity to be administered depends on the subject to be treated, including, e.g., the capacity of the host's immune system to synthesize antibodies, and the degree of protection desired. Precise amounts of the transformed cells required will depend to some extent on the judgment of the practitioner and the age, health, sex, etc., of the host. However, suitable dose ranges may be determined from animal models and initial clinical studies. Generally, it is contemplated that on the order of $10^6$ transformed cells will be required.

Adjuvants may be preferred in cases where the host immune system is weakened or compromised. Adjuvants commonly used include agents such as aluminum hydroxide or phosphate (alum), admixture with synthetic polymers of sugars (Carbopol®), aggregation of protein in the vaccine by heat treatment (e.g. 70-101 degrees C.) Aggregation by reactivating with pepsin treated (Fab) antibodies to albumin, mixture with bacterial cells such as *C. parvum* or endotoxins or lipopolysaccharide components of Gram-negative bacteria, emulsion in physiologically acceptable vegetable oils vehicles such as mannide mono-oleate (Aracel A) or emulsion with a 20% solution of perfluorocarbon (Fluosol-DA®) used as a block substitute may also be employed. Other adjuvants are well known in the field.

In certain instances, it will be desirable to administer multiple doses of the vaccine, usually not exceeding ten vaccinations, more usually not exceeding four and preferably one or more, usually two or three. The vaccinations will normally be at from two to twelve week intervals, more usually from three to five weeks. Periodic boosters at intervals of 1-5 years, usually three years, may be required to maintain a protective level of antibodies and memory T cells.

Pharmaceutical Vaccine Compositions

Pharmaceutical compositions containing the cancer cell vaccine are preferably administered parenterally, intraperitoneally, intradermally or intramuscularly. Pharmaceutical forms suitable for injection include sterile aqueous solutions or dispersions for extemporaneous preparation of the solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained by the use of a coating such as lecithin, by the maintenance of the required particle size in case of a dispersion and by the use of surfactants. The prevention of the action of microorganisms can be effected by various antibacterial and antifungal agents such as parabens, chlorobutanol, phenol, sorbic acid, thimerosal and the like. In many cases, isotonic agents may be included, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

Upon formulation, solutions will be administered in a manner compatible with the dosage formulation and in such amount as is therapeutically effective. The formulations are easily administered in a variety of dosage forms preferably as injectable solutions.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intradermal and intraperitoneal administration. In this connection, sterile aqueous media that can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Drug Discovery

Another use of human cancer stem cells is related to drug discovery. Because the isolated human cancer stem cell populations disclosed herein and those obtained following the teaching of this invention have not been previously isolated or cultured in the disclosed manner, they are novel and may display on their surface, express or secrete proteins that have not been heretofore discovered or characterized. Previous culturing techniques using serum may inhibit the display of proteins on the cell surface and/or the secretion of proteins. Additionally, serum proteins or serum biomolecules may cause a change in the CSC phenotype, and bind to the cancer stem cell surface and interfere with raising monoclonal antibodies to endogenous CSC antigens. Alternatively, proteins may change in function, conformation, or activity as they are being secreted and interacting with serum biomolecules. Proteins displayed or secreted by human cancer stem cells grown in a defined serum-free media have minimal interference from serum biomolecules and thus, may be more physiologically and topologically accurate. Therefore, proteins expressed, secreted by or displayed on the surface of a human cancer stem cell are desirable targets for drug development. In one embodiment, drugs are made that target specific proteins on human cancer stem cells and/or cells treated or differentiated therefrom in vivo. Binding of the drug may alter the growth capacity of the human cancer stem cells. In yet another embodiment, human cancer stem cells are used to develop or discover small molecules or other therapeutic agents that interact with human tumor cells. These small molecules may be synthetic or natural and can be used to stop, inhibit or promote the growth of human tumor cells.

Methods of Treatment

Another aspect of the invention involves treating a disease condition with a cancer stem cell (entire or partial), or a modulator (including but not limited to antibodies) of a target antigen that is present on the surface of the tumor stem cells of this invention.

In another aspect, the present invention provides a method comprising administering to a subject diagnosed with a disease an amount of a radiotherapeutic agent, and a CSC or a modulator of a CSC cell surface antigen. In preferred embodiments, the radiotherapeutic agent is selected from the group consisting of radioactive isotopes (e.g. $At^{-211}$, $I^{-131}$, $I^{-125}$, $Y^{-90}$, $Re^{-186}$, $Re^{-188}$, $Sm^{-153}$, $Bi^{-212}$, $P^{-32}$ and radioactive isotopes of Lu), although in other embodiments other agents are administered, such as chemotherapeutic agents, toxins such as small molecule toxins or enzymatically active toxins of bacterial, fungal, plant or animal origin, including fragments and/or variants thereof, free radicals, electric charge, ischemia, oxidant injury, heat shock, cardiac hypertrophy, fever, inflammation, metabolic diseases, infection, cytokines, growth factors, hormones, pathogens, (e.g., bacteria, parasites, intracellular parasites, fungi, viruses, prions, and viroids), cell-cell interactions, soluble factors, and cell and tissue damage of other causes.

The subject treatment methods can employ a variety of therapeutic compositions disclosed herein, or in combination with any known treatment in the art. In one embodiment, the antibody populations and/or the hybridomas producing such antibodies are used for the treatment of a disease condition.

In another embodiment, the therapeutic compositions of this invention are effective in making the diseased or damaged cells more susceptible to complement dependent cytotoxicity (CDC), antibody dependent cell mediated cytotoxicity (ADCC) or other host surveillance immunity.

In another embodiment, therapeutic compositions of this invention are used in combination with other agents of the same or different classification. The combination treatments can occur in concert or one treatment may precede the other. Subjects in need of thereof can cycle to different therapeutic compositions at different time points of their treatment.

Another aspect of the invention involves personalized treatment with the therapeutic compositions of the invention, in which the antigen(s) expressed on the diseased cells of a subject are determined, and then the therapeutic composition of this invention that modulates a particular subject antigen is then administered to the subject according to the methods described herein. In one embodiment, the therapeutic compositions of the present invention are used for the personalized treatment.

Treatment of Neoplastic Conditions

Neoplastic conditions include benign or malignant tumors (e.g., renal, liver, kidney, bladder, breast, gastric, ovarian, colorectal, prostate, pancreatic, lung, vulval, thyroid, hepatic carcinomas; sarcomas; glioblastomas; and various head and neck tumors); leukemias and lymphoid malignancies; other disorders such as neuronal, glial, astrocytal, hypothalamic and other glandular, macrophagal, epithelial, stromal and blastocoelic disorders; and inflammatory, angiogenic, immunologic disorders and disorders caused by pathogens. Particularly preferred targets for treatment with therapeutic compositions and methods of the present invention are neoplastic conditions.

The invention provides methods to treat several specific neoplastic conditions. In certain embodiments, the neoplastic conditions are selected from the group including but not limited to adrenal gland tumors, AIDS-associated cancers, alveolar soft part sarcoma, astrocytic tumors, bladder cancer (squamous cell carcinoma and transitional cell carcinoma), bone cancer (adamantinoma, aneurismal bone cysts, osteochondroma, osteosarcoma), brain and spinal cord cancers, metastatic brain tumors, breast cancer, carotid body tumors, cervical cancer, chondrosarcoma, chordoma, chromophobe renal cell carcinoma, clear cell carcinoma, colon cancer, colorectal cancer, cutaneous benign fibrous histiocytomas, desmoplastic small round cell tumors, ependymomas, Ewing's tumors, extraskeletal myxoid chondrosarcoma, fibrogenesis imperfecta ossium, fibrous dysplasia of the bone, gallbladder and bile duct cancers, gestational trophoblastic disease, germ cell tumors, head and neck cancers, islet cell tumors, Kaposi's Sarcoma, kidney cancer (nephroblastoma, papillary renal cell carcinoma), leukemias, lipoma/benign lipomatous tumors, liposarcoma/malignant lipomatous tumors, liver cancer (hepatoblastoma, hepatocellular carcinoma), lymphomas, lung cancers (small cell carcinoma, adenocarcinoma, squamous cell carcinoma, large cell carcinoma etc.), medulloblastoma, melanoma, meningiomas, multiple endocrine neoplasia, multiple myeloma, myelodysplastic syndrome, neuroblastoma, neuroendocrine tumors, ovarian cancer, pancreatic cancers, papillary thyroid carcinomas, parathyroid tumors, pediatric cancers, peripheral nerve sheath tumors, phaeochromocytoma, pituitary tumors, prostate cancer, posterious unveal melanoma, rare hematologic disorders, renal metastatic cancer, rhabdoid tumor, rhabdomysarcoma, sarcomas, skin cancer, soft-tissue sarcomas, squamous cell cancer, stomach cancer, synovial sarcoma, testicular cancer, thymic carcinoma, thymoma, thyroid metastatic cancer, and uterine cancers (carcinoma of the cervix, endometrial carcinoma, and leiomyoma). In certain preferred embodiments, the cancerous cells are selected from the group of solid tumors including but not limited to breast cancer, colon cancer, prostate cancer, lung cancer, sarcoma, renal metastatic cancer, thyroid metastatic cancer, and clear cell carcinoma.

Carcinoma of the thyroid gland is the most common malignancy of the endocrine system. Carcinoma of the thyroid gland includes differentiated tumors (papillary or follicular) and poorly differentiated tumors (medullary or anaplastic). Carcinomas of the vagina include squamous cell carcinoma, adenocarcinoma, melanoma and sarcoma. Testicular cancer is broadly divided into seminoma and nonseminoma types.

Thymomas are epithelial tumors of the thymus, which may or may not be extensively infiltrated by nonneoplastic lymphocytes. The term thymoma is customarily used to describe neoplasms that show no overt atypia of the epithelial component. A thymic epithelial tumor that exhibits clear-cut cytologic atypia and histologic features no longer specific to the thymus is known as a thymic carcinoma (also known as type C thymoma).

In one preferred embodiment, the invention provides a method of treating breast cancer such as a ductal carcinoma in duct tissue in a mammary gland, medullary carcinomas, colloid carcinomas, tubular carcinomas, and inflammatory breast cancer. Existing treatments available for these breast cancers patients are surgery, immunotherapy, radiation therapy, chemotherapy, endocrine therapy, or a combination thereof. The subject therapeutic compositions can be administered after the subject has been treated with any of these treatments or a combination thereof. In certain embodiments, the subject therapeutic compositions can be administered after the subject has been treated with one or more chemotherapeutic regimens such as doxorubicin, cyclophosphamide, methotrexate, paclitaxel, thiotepa, mitoxantrone, vincristine, or combinations thereof. In other embodiments, the subject therapeutic compositions can be administered after the subject has been treated with one or more agents for endocrine therapy such as tamoxifen, megestrol acetate, aminoglutethimide, fluoxymesterone, leuprolide, goserelin, and prednisone.

In another embodiment, the present invention provides a treatment for ovarian cancer, including epithelial ovarian tumors such as adenocarcinoma in the ovary and an adenocarcinoma that has migrated from the ovary into the abdominal cavity. The subject therapeutic compositions can be administered after the subject has been treated with any of the existing treatments including immunotherapy, radiation therapy, chemotherapy, endocrine therapy or a combination thereof. In certain embodiments, the therapeutic compositions can be administered after the subject has been treated with one or more chemotherapeutic regimens such as cyclophosphamide, etoposide, altretamine, and ifosfamide. In other embodiments, the subject therapeutic compositions can be administered after the subject has been treated with one or more hormone therapy agents such as tamoxifen.

Additionally, the invention provides a method of treating cervical cancer such as adenocarcinoma in the cervix epithelial including squamous cell carcinoma and adenocarcinomas. The chief treatments available for cervical cancer are surgery (cryosurgery, a hysterectomy, and a radical hysterectomy), immunotherapy, radiation therapy (external beam radiation therapy or brachytherapy) and chemotherapy. In certain embodiments, the subject therapeutic compositions can be administered after the subject has been treated with one or more chemotherapeutic regimens such as cisplatin, carboplatin, hydroxyurea, irinotecan, bleomycin, vincristine, mitomycin, ifosfamide, fluorouracil, etoposide, methotrexate, or a combination thereof.

The invention also provides a treatment for prostate cancer, such as a prostate cancer selected from the following: an adenocarcinoma or an adenocarcinoma that has migrated to the bone. Surgery, immunotherapy, radiation therapy, cryosurgery, hormone therapy, and chemotherapy are some treatments available for prostate cancer patients. Some radiation therapy options are external beam radiation, including three dimensional conformal radiation therapy, intensity modulated radiation therapy, and conformal proton beam radiation therapy. Brachytherapy and cryosurgery are other possible methods used to treat prostate cancer. The subject therapeutic compositions can be administered after the subject has been treated with any of these treatments or a combination thereof.

In certain embodiments, the subject therapeutic compositions can be administered after the subject has been treated with one or more hormone therapy agents including luteinizing hormone-releasing hormone (LHRH) analogs such as leuprolide, goserelin, triptorelin, and histrelin, and LHRH antagonist such as abarelix. In other embodiments, the subject therapeutic compositions can be administered after the subject has been subjected to androgen deprivation therapy or androgen suppression therapy including orchiectomy. In other embodiments, the subject therapeutic compositions can be administered after the subject has been treated with an anti-androgen agent such as flutamide, bicalutamide, and nilutamide. In other embodiments, the subject therapeutic compositions can be administered after the subject has been treated with one or more chemotherapeutic agents such as doxorubicin, estramustine, etoposide, mitoxantrone, vinblastine, paclitaxel, docetaxel, carboplatin, prednisone or a combination thereof.

The present invention further provides methods of treating pancreatic cancer such as epithelioid carcinoma in the pancreatic duct tissue and an adenocarcinoma in a pancreatic duct. The subject therapeutic compositions can be administered after the subject has been treated with any of the existing treatments including chemotherapy and radiation, or a combination thereof. The subject therapeutic compositions can be administered after the subject has been treated with one or more chemotherapeutic agents such as 5-fluorouracil (5-FU), mitomycin, ifosfamide, doxorubicin, steptozocin, chlorozotocin, or combinations thereof.

The present invention provides additional methods of treating bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers. In certain embodiments, the subject therapeutic compositions can be administered after the subject has been treated with one or more immunotherapy agents such as Bacillus Calmete-Guerin (BCG), interferons, and glycoproteins. In other embodiments, the subject therapeutic compositions can be administered after the subject has been treated with one or more chemotherapeutic agents such as thitepa, methotrexate, vinblastine, doxorubicin, cyclophosphamide, paclitaxel, carboplatin, cisplatin, ifosfamide, gemcitabine, or combinations thereof.

Moreover, the present invention provides a treatment for lung cancer such as non-small cell lung cancer (NSCLC), which is divided into squamous cell carcinomas, adenocarcinomas, and large cell undifferentiated carcinomas, and small cell lung cancer. Treatment options for lung cancer include surgery, immunotherapy, radiation therapy, chemotherapy, photodynamic therapy, or a combination thereof. Some possible surgical options for treatment of lung cancer are a segmental or wedge resection, a lobectomy, or a pneumonectomy. Radiation therapy may be external beam radiation therapy or brachytherapy. In certain embodiments, the subject therapeutic compositions can be administered before, after, or concurrently with treatment of a subject with one or more chemotherapeutic agents such as cisplatin, carboplatin, paclitaxel, docetaxel, gemcitabine, vinorelbine, irinotecan, etoposide, vinblastine, gefitinib, ifosfamide, methotrexate, or a combination thereof.

The subject treatment methods can be particularly effective in inhibiting growth of a neoplastic cell, especially for those neoplastic cells that have been previously exposed to an anti-cancer agent. The subject methods can also be effective in maintaining or increasing cell susceptibility to an anti-cancer therapeutic agent.

The invention provides methods to treat several specific natural and induced immune deficiency states. For example, natural and induced immune deficiency states include B cell (antibody) deficiencies, combined T cell and B cell (antibody) deficiencies, T cell deficiencies, defective phagocytes, complement deficiencies and deficiencies due to the administration of immunosuppressants.

Methods of Administration

The therapeutic compositions of the present invention are administered to a mammal, preferably a human in accord with known methods, such as intravenous administration as a bolus or by continuous infusion over a period of time, by intramuscular, intraperitoneal, transmucosal, intracerebrospinal, subcutaneous, intra-articular, intrasynovial, intrathecal, oral, topical, or inhalation routes. Intravenous administration of antibodies is preferred. The therapeutic compositions of the present invention can be administered as described above in combination with a therapeutic treatment, e.g., chemotherapeutic agent. The therapeutic agent can be administered by the same of different routes of administration.

The therapeutic treatment may precede or follow the treatment with the antigen modulator, or may occur simultaneously. The effective amount of a therapeutic agent can be determined by routine testing. Co-administration includes simultaneous administration, or consecutive administration of the two agents in either order.

Administration in combination can include simultaneous administration of two or more agents in the same dosage form, simultaneous administration in separate dosage forms, and separate administration. That is, the subject therapeutic composition and another therapeutic agent can be formulated together in the same dosage form and administered simultaneously. Alternatively, subject therapeutic composition and another therapeutic agent can be simultaneously administered, wherein both the agents are present in separate formulations. In another alternative, the therapeutic agent can be administered just followed by the other therapeutic agent or vice versa. In the separate administration protocol, the subject therapeutic composition and another therapeutic agent may be administered a few minutes apart, or a few hours apart, or a few days apart.

Regarding neoplastic condition treatment, depending on the stage of the neoplastic condition, neoplastic condition treatment involves one or a combination of the following therapies: surgery to remove the neoplastic tissue, radiation therapy, and chemotherapy. The treatment methods of the present invention improve the therapeutic index of therapeutic agents, such as chemotherapy, and thereby allow the reduction of the effective dose to be administered. Accordingly, the therapeutic methods herein are especially useful in the treatment of elderly patients and others who do not tolerate well the toxicity and side effects of chemotherapy and in metastatic disease where radiation therapy has limited usefulness.

Other therapeutic regimens may be combined with the administration of the anti-cancer agents, e.g., therapeutic compositions and chemotherapeutic agents. For example, the patient to be treated with such anti-cancer agents may also receive radiation therapy and/or may undergo surgery.

For the prevention or treatment of disease, the appropriate dosage of an therapeutic composition, e.g., an antibody herein will depend on the type of disease to be treated, as defined above, the severity and course of the disease, whether the agent is administered for preventive or therapeutic purposes, previous therapy, the patient's clinical history and response to the agent, and the discretion of the attending physician. The agent is suitably administered to the patient at one time or over a series of treatments.

Formulations

Various formulations of the therapeutic compositions of this invention may be used for administration. In some embodiments, therapeutic compositions may be administered neat. In addition to the pharmacologically active agent, the compositions of the present invention may contain suitable pharmaceutically acceptable carriers comprising excipients and auxiliaries that are well known in the art and are relatively inert substances that facilitate administration of a pharmacologically effective substance or which facilitate processing of the active compounds into preparations that can be used pharmaceutically for delivery to the site of action. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers.

Suitable formulations for parenteral administration include aqueous solutions of the active compounds in water-soluble form, for example, water-soluble salts. In addition, suspensions of the active compounds as appropriate for oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances that increase the viscosity of the suspension and include, for example, sodium carboxymethyl cellulose, sorbitol, and/or dextran. Optionally, the suspension may also contain stabilizers. Liposomes can also be used to encapsulate the agent for delivery into the cell.

The pharmaceutical formulation for systemic administration according to the invention may be formulated for enteral, parenteral or topical administration. Indeed, all three types of formulation may be used simultaneously to achieve systemic administration of the active ingredient. Excipients as well as formulations for parenteral and nonparenteral drug delivery are set forth in Remington, The Science and Practice of Pharmacy 20th Ed. Mack Publishing (2000).

Suitable formulations for oral administration include hard or soft gelatin capsules, pills, tablets, including coated tablets, elixirs, suspensions, syrups or inhalations and controlled release forms thereof.

Generally, these agents are formulated for administration by injection (e.g., intraperitoneally, intravenously, subcutaneously, intramuscularly, etc.), although other forms of administration (e.g., oral, mucosal, etc) can be also used. Accordingly, therapeutic compositions are preferably combined with pharmaceutically acceptable vehicles such as saline, Ringer's solution, dextrose solution, and the like.

The particular dosage regimen, i.e., dose, timing and repetition, will depend on the particular individual and that individual's medical history. Generally regarding antibodies, a dose of at least about 100 ug/kg body weight, more preferably at least about 250 ug/kg body weight, even more preferably at least about 750 ug/kg body weight, even more preferably at least about 3 mg/kg body weight, even more preferably at least about 5 mg/kg body weight, even more preferably at least about 10 mg/kg body weight is administered.

Empirical considerations, such as the half-life, generally will contribute to the determination of the dosage. Regarding antibodies, which are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is based on reducing the number of neoplastic cells, maintaining the reduction of neoplastic cells, reducing the proliferation of neoplastic cells, or delaying the development of metastasis. Alternatively, sustained continuous release formulations of a subject therapeutic composition may be appropriate. Various formulations and devices for achieving sustained release are known in the art.

In one embodiment, dosages for therapeutic compositions may be determined empirically in individuals who have been given one or more administration(s). Individuals are given incremental dosages of a therapeutic composition produced as described herein. To assess efficacy antibodies, a marker of the specific disease, disorder or condition can be followed. In embodiments where the individual has cancer, these include direct measurements of tumor size via palpation or visual observation, indirect measurement of tumor size by x-ray or other imaging techniques; an improvement as assessed by direct tumor biopsy and microscopic examination of the tumor sample; the measurement of an indirect tumor marker (e.g., PSA for prostate cancer) or an antigen identified according to the methods described herein, a decrease in pain or paralysis; improved speech, vision, breathing or other disability associated with the tumor; increased appetite; or an increase in quality of life as measured by accepted tests or prolongation of survival. It will be apparent to one of skill in the art that the dosage will vary depending on the individual, the type of neoplastic condition, the stage of neoplastic condition, whether the neoplastic condition has begun to metastasize to other location in the individual, and the past and concurrent treatments being used.

Other formulations include suitable delivery forms known in the art including, but not limited to, carriers such as liposomes. Liposomal preparations include, but are not limited to, cytofectins, multilamellar vesicles and unilamellar vesicles.

In some embodiments, more than one therapeutic composition may be present. Such compositions may contain at least one, at least two, at least three, at least four, at least five different therapeutic composition.

Articles of Manufacture

In another embodiment of the invention, an article of manufacture containing the therapeutic composition herein, alone or in combination with a therapeutic or conditioning agent, are provided. The article of manufacture comprises a container and a label. Suitable containers include, for example, bottles, vials, syringes, and test tubes. The containers may be formed from a variety of materials such as glass or plastic. The container holds a composition that is effective for treating a disease condition targeted and may have a sterile access port (for example the container may be an intravenous solution bag or a vial having a stopper pierceable by a hypodermic injection needle). The active agent in the composition is an antigen modulator, preferably an antibody. The label on, or associated with, the container indicates that the composition is used for diagnosing or treating the disease condition of choice. The article of manufacture will further comprise, within the same or a separate container, a therapeutic agent and optionally a pharmaceutically acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

Xenograft Models

Another use for human cancer stem cells is to create human tissue models in non-human mammals. In some embodiments, human cancer stem cells are placed under the kidney capsule of a xenograft recipient and allowed to grow. In another embodiment, human cancer stem cells are placed subcutaneously in a recipient animal and allowed to grow. A skilled artisan can determine the optimal combination in a stepwise fashion, by first isolating human cancer stem cells using the methods disclosed herein and then implanting them in the desired xenograft site.

In another embodiment, the human cancer stem cells are placed in an orthotopic site in a recipient animal. A skilled artisan can determine the optimal combination in a stepwise fashion, by first isolating human cancer stem cells using the methods disclosed herein and then implanting them in the desired orthopic site. Examples of this procedure are well known in the art including by way of a non-limiting example, placing breast cancer stem cells in a mammary fat pad.

Human cancer stem cells used for xenografts can be first combined with a substrate. Many suitable substrates are well known in the art and include, but not limited to fibronectin, Matrigel, collagen and laminin. Suitable recipient mammals include but are not limited to mice and rats. Typically in graft situations, donor tissue is vulnerable to attack by the recipient's immune system. To alleviate graft rejection, several techniques are used. One method is to irradiate the recipient with a sub-lethal dose of radiation to destroy immune cells that may attack the graft. Another method is to give the recipient cyclosporin or other T cell immunosuppressive drugs. With the use of mice as recipient mammals, a wider variety of methods are possible for alleviating graft rejection. One such method is the use of an immunodeficient mouse (nude or severe combined immunodeficiency or SCID). Human cancer stem cell xenografts can be used to study tumor formation and/or growth in vivo or used in drug discovery or development.

Bioassays

The human cancer stem cells disclosed herein can be used in various bioassays. In one embodiment, the human cancer stem cells are used to determine which biological factors impact the growth capacity of the human cancer stem cells. By evaluating cancer stem cells in a stepwise fashion in combination with different biological compounds (such as hormones, specific growth factors, etc.), one or more specific biological compounds can be found that induce an alteration or change in the growth capacity or potential of the human cancer stem cell.

Other uses in a bioassay for cancer stem cells are differential display (e.g., mRNA differential display) and protein-protein interactions using secreted proteins from cancer stem cells. Protein-protein interactions can be determined with techniques such as yeast two-hybrid system. Proteins from human cancer stem cells can be used to identify other unknown proteins or other cell types that interact with cancer stem cells. These unknown proteins may be one or more of the following: growth factors, hormones, enzymes, transcription factors, translational factors, and tumor suppressors. Bioassays involving human cancer stem cells and the protein-protein interaction these cells form and the effects of protein-protein or even cell-cell contact may be used to determine how these cells contribute to the establishment, growth and formation of tumors in vivo. The following examples provide a detailed description of the isolation, characterization, and use of human cancer stem cells. These examples are not intended to limit the invention in any way.

EXAMPLES

Example 1

Isolation and Culturing of Colorectal Carcinoma Cells (CRCA)

Tissue from a colorectal carcinoma was briefly rinsed in sterile phosphate buffered saline (PBS) containing 100 µg/mL gentamycin, placed in a 100 mm tissue culture dish, and minced into small (<1 mm) pieces. The minced tissue was suspended in 5 mL of dissociation media (F12/DMEM containing 100 µg/mL gentamycin and 200 µL collagenase-dispase (10% wt/vol in PBS) with soybean trypsin inhibitor (STI, 10% (v/v)) and incubated at 37° C. At 5-minute intervals, the suspension was pipetted to loosen cell aggregates. Enzymatic activity was stopped when aggregates of 10-20 cells appeared dissociated from the tissue.

The suspension was washed with F12/DMEM by centrifugation (4 minutes at 900 rpm) and the resulting cell pellet was resuspended in culture medium (serum free F12/DMEM supplemented with insulin (10 µg/mL), transferrin (10 µg/mL), epidermal growth factor (EGF) (5 ng/mL), selenium ($2.5 \times 10^{-8}$M), triiodothyronine (T3) ($1 \times 10^{-12}$M), ethanolamine ($1 \times 10^{-6}$M), phosphoethanolamine ($1 \times 10^{-6}$ M), hydrocortisone ($5 \times 10^{-8}$M), vitamin E (5 µg/mL), and optionally gentamycin (50 µg/mL)).

The cell suspension was transferred and divided into five 100 mm laminin or fibronectin-coated dishes. Culture medium was added for a final volume of 10 mL per dish and the dishes were incubated at standard incubation conditions.

The colorectal carcinoma stem cells grew in loose clusters and have an epithelial cellular morphology. As compared to the other cells in culture, the colorectal carcinoma stem cells were much smaller in size and therefore were further distinguished using this morphological feature. When initially placed into culture, the cells from the colorectal carcinoma tissue attached quickly (8-24 hours) to the culture dish. Medium was changed regularly (preferably every 3 days) and the cultures observed under a microscope until the small densely packed stem cell colonies could be seen. After several weeks, small, loose clusters of colorectal carcinoma stem cells were visible. The colorectal carcinoma stem cells immediately began to grow at an exponential rate and after about an additional 2 weeks in culture, the cells could be subcultured in the same medium to obtain a substantially purified culture of colorectal carcinoma stem cells which can be continuously subcultured in the same medium as an established cell line. At this point, the colorectal carcinoma stem cells were split and passaged using standard techniques known in the art using collagenase-dispase to lift the cells from the culture dish, without digesting to the point of single cells. One colorectal carcinoma stem cell culture has been passaged over 30 times without signs of senescence.

Example 2

Isolation and Culturing of Rectal Carcinoma Cells (RECA)

Tissue from a rectal carcinoma was briefly rinsed in sterile phosphate buffered saline (PBS) containing 100 µg/mL gentamycin, placed in a 100 mm tissue culture dish, and minced into small (<1 mm) pieces. The minced tissue was suspended in 5 mL of dissociation media (F12/DMEM containing 100 µg/mL gentamycin and 200 µL collagenase-dispase (10% wt/vol in PBS) with soybean trypsin inhibitor (STI, 10%(v/ v)) and incubated at 37° C. At 5-minute intervals, the suspension was pipetted to loosen cell aggregates. Enzymatic activity was stopped when aggregates of 10-20 cells appeared dissociated from the tissue.

The suspension was washed with F12/DMEM by centrifugation (4 minutes at 900 rpm) and the resulting cell pellet was resuspended in culture medium (serum free F12/DMEM supplemented with insulin (10 µg/mL), transferrin (10 µg/mL), EGF (5 ng/mL), selenium ($2.5 \times 10^{-8}$M), T3 ($1 \times 10^{-9}$M), ethanolamine ($1 \times 10^{-6}$M), phosphoethanolamine ($1 \times 10^{-6}$M), hydrocortisone ($5 \times 10^{-8}$ M), vitamin E (5 µg/mL), and porcine pituitary extract (PPE) (75 µg total protein of PPE/mL).

The cell suspension was transferred and divided into five 100 mm laminin/fibronectin (50:50)-coated dishes. Culture medium was added for a final volume of 10 mL per dish and the dishes were incubated at standard incubation conditions described above for the colon cancer cultures. After the stem cells had arisen and been selected by subculture in the described medium the line can be carried as follows. The growth media was changed every 2-3 days until the cells were 80-95% confluent and was ready to be subcultured. The human rectal carcinoma stem cells were passaged using standard conditions known in the art using collagenase-dispase to lift the cells from the culture dishes. One rectal carcinoma stem cell line has been passaged over 50 times without signs of senescence.

Example 3

Isolation and Culturing of Lung Carcinoma Stem Cells

Tissue from a lung adenocarcinoma was briefly rinsed in sterile phosphate buffered saline (PBS) containing 100 µg/mL gentamycin, placed in a 100 mm tissue culture dish, and minced into small (<1 mm) pieces. The minced tissue was suspended in 5 mL of dissociation media (F12/DMEM containing 100 µg/mL gentamycin and 200 µL collagenase-dispase (10% wt/vol in PBS) with soybean trypsin inhibitor (STI, 10%(v/v)) and incubated at 37° C. At 5-minute intervals, the suspension was pipetted to loosen cell aggregates. Enzymatic activity was stopped when aggregates of 10-20 cells appeared dissociated from the tissue.

The suspension was washed with F12/DMEM by centrifugation (4 minutes at 900 rpm) and the resulting cell pellet was resuspended in culture medium (serum free F12/DMEM supplemented with insulin (10 µg/mL), EGF (5 ng/mL), selenium ($2.5 \times 10^{-8}$M), bovine pituitary extract (BPE) or PPE (75 µg total protein of PPE/mL).

The cell suspension was transferred and divided into five 100 mm fibronectin-coated dishes. Culture medium was added for a final volume of 10 mL per dish and the dishes were incubated at standard incubation conditions.

The growth media was changed every 2-3 days until the cells were 80-95% confluent and was ready to be subcultured. The human lung carcinoma stem cells were passaged using standard conditions known in the art using collagenase-dispase to lift the cells from the culture dishes. One human lung carcinoma stem cell culture has been passaged over 25 times without signs of senescence.

Example 4

Isolation and Culturing of Pancreatic Ductal Carcinoma Stem Cells

Tissue from a pancreatic ductal carcinoma was briefly rinsed in sterile phosphate buffered saline (PBS), placed in a 100 mm tissue culture dish, and minced into small (<1 mm) pieces. The minced tissue was suspended in 5 mL of dissociation media (F12/DMEM containing 100 µg/mL gentamycin and 200 µL collagenase-dispase (10% wt/vol in PBS) with soybean trypsin inhibitor (STI, 10%(v/v)) and incubated at 37° C. At 5-minute intervals, the suspension was pipetted to loosen cell aggregates. Enzymatic activity was stopped when aggregates of 10-20 cells appeared dissociated from the tissue.

The suspension was washed with F12/DMEM by centrifugation (4 minutes at 900 rpm) and the resulting cell pellet was resuspended in culture medium (serum free F12/DMEM supplemented with insulin (10 µg/mL), transferrin (10 µg/mL), EGF (5 ng/mL), selenium ($2.5 \times 10^{-8}$M), T3 ($1 \times 10^{-2}$M), ethanolamine ($1 \times 10^{-6}$M), phosphoethanolamine ($1 \times 10^{-6}$M), forskolin (1-5 µM), hydrocortisone ($1 \times 10^{-9}$M), progesterone ($1 \times 10^{-8}$M), heregulin (HRG) (1-3 nM), and aprotinin (25 µg/mL)).

The cell suspension was transferred and divided into three 100 mm fibronectin-coated (5 µg/mL) dishes. Culture medium was added for a final volume of 10 mL per dish and the dishes were incubated at standard incubation conditions. Every 3 days, the spent medium was collected, filtered with a 0.22 µm filter, and added (20% vol/vol) to reconstitute the cells. Within 7-10 days of initial plating, only a few epithelial-like colonies formed and these colonies began to spread among the non-dividing stromal-like cells. Within another 14 days, the cultures were subcultured at subconfluence and split 1:3 in fibronectin-coated 100 mm dishes using standard methods known in the art. After the pancreatic ductal carcinoma stem cells were established in culture (after the second or third passage), the use of conditioned media from previous cultures were no longer necessary. One skilled in the art would be able to determine when the use of conditioned medium would no longer be required based on observing the growth and appearance of the cells. Aprotinin was no longer added to the culture medium when no further growth stimulation was observed in the presence of this factor. Subsequent growth studies indicated a doubling time of 26 hours. One pancreatic ductal carcinoma stem cell culture has been passaged over 60 times without signs of senescence.

Example 5

Isolation and Culturing of Merkel Cell Carcinoma Stem Cells

Tissue from a Merkel cell carcinoma was briefly rinsed in sterile phosphate buffered saline (PBS) containing 100 µg/mL gentamycin, placed in a 100 mm tissue culture dish, and minced into small (<1 mm) pieces. The minced tissue was suspended in 5 mL of dissociation media (F12/DMEM containing 100 µg/mL gentamycin and 200 µL collagenase-dispase (10% wt/vol in PBS) with soybean trypsin inhibitor (STI, 10%(v/v)) and incubated at 37° C. At 5-minute intervals, the suspension was pipetted to loosen cell aggregates. Enzymatic activity was stopped when aggregates of 10-20 cells appeared dissociated from the tissue.

The suspension was washed with F12/DMEM by centrifugation (4 minutes at 900 rpm) and the resulting cell pellet was resuspended in culture medium (serum free F12/DMEM supplemented with insulin (10 µg/mL), transferrin (10 µg/mL), EGF (5 ng/mL), selenium ($2.5 \times 10^{-8}$M), T3 ($1 \times 10^{-12}$M), ethanolamine ($1 \times 10^{-6}$M), phosphoethanolamine ($1 \times 10^{-6}$M), forskolin (5 µM), hydrocortisone ($1 \times 10^{-9}$M), progesterone ($1 \times 10^{-8}$M), PPE (15 µg total protein of PPE). Some cultures of Merkel cell carcinoma stem cells do not require PPE for growth after the culture has been established. This can be tested after the third or fourth passage of the Merkel cell carcinoma stem cell culture. In some cases, the addition of nerve growth factor β (NGF-β) may be advantageous to the growth of the Merkel cell carcinoma stem cell culture. NGF-β may be used at 10 ng/ml concentration after the culture has been established.

Figure 1:
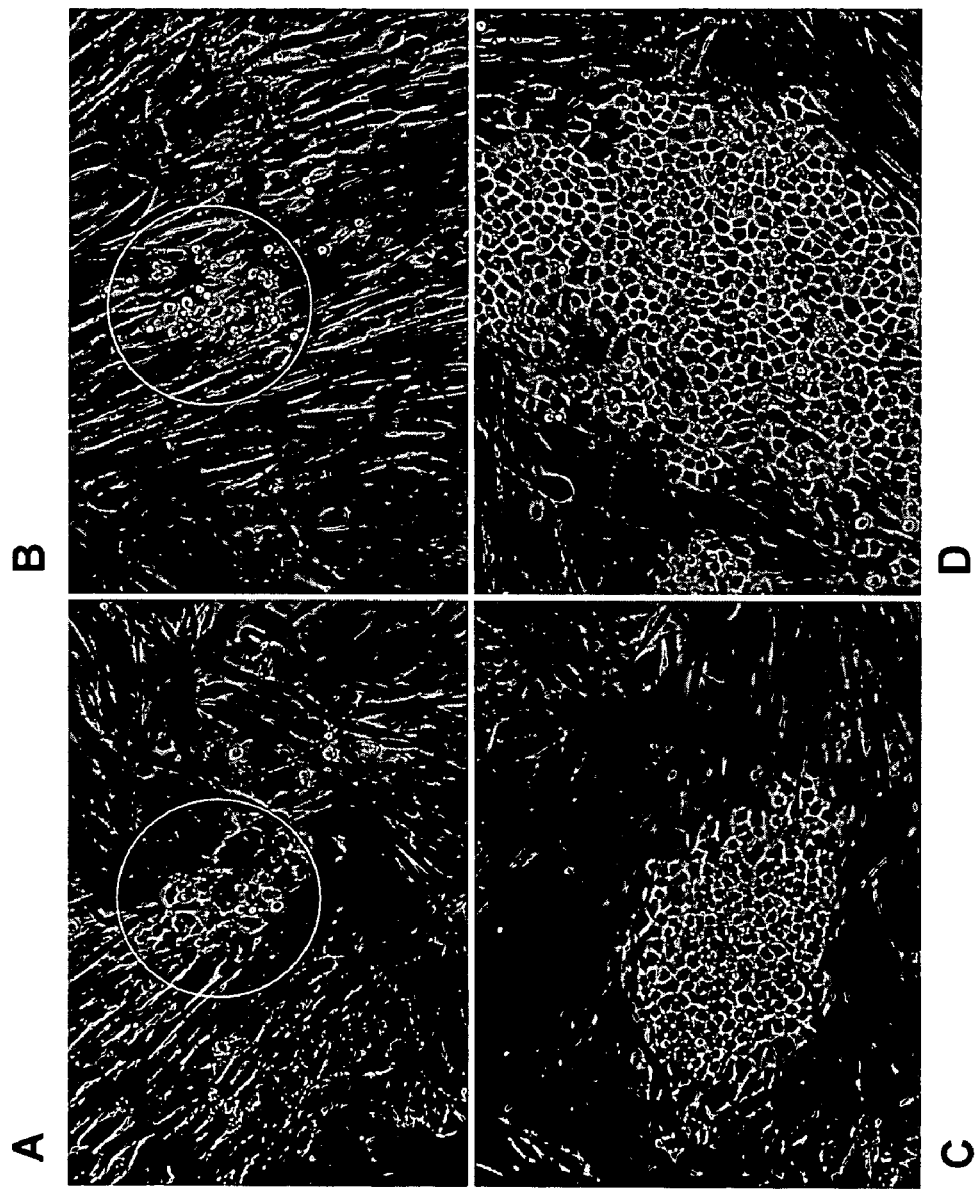
FIG. 1 shows selective growth of CSC colonies from prostate carcinoma tumor (PRCA) using a defined cell culture medium.
Figure 2:
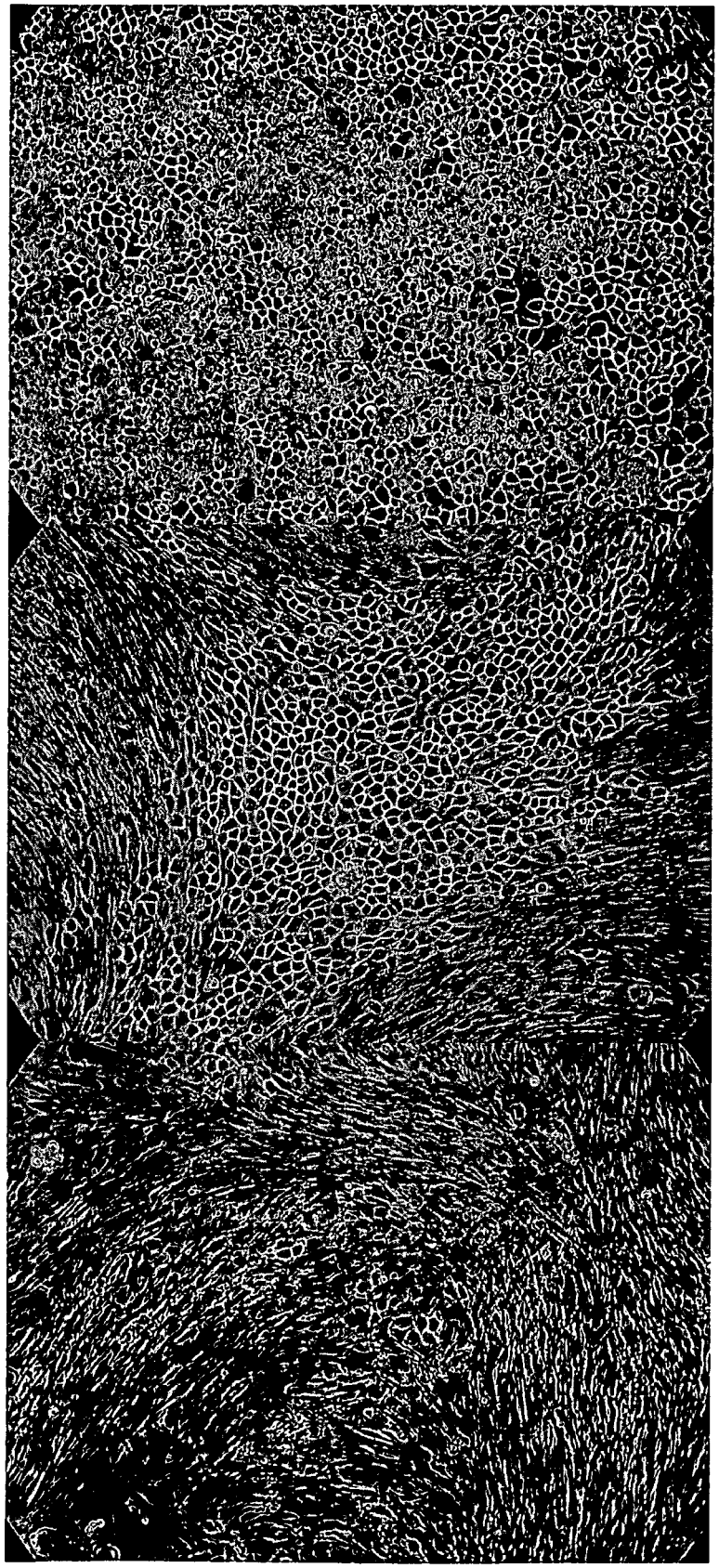
FIG. 2 shows a set of CSC colonies derived from basal cell carcinoma (BCCA1) cultured in the defined medium selective for this cancer stem cell type.

The cell suspension was transferred and divided into five fibronectin-coated 100 mm dishes. Culture medium was added for a final volume of 10 mL per dish and the dishes were incubated at standard incubation conditions with a medium change every 3 days until the stem cell colonies become apparent (see FIGS. 1-3). At this point most of the non-stem cells have died and the stem cell colonies can be grown up to a sufficient cell density (@ 50%) to subculture at a density of 1:3.

Once the Merkel cell carcinoma stem cell culture was about 85-95% confluent, the culture was sub-cultured using TrypLE Express (Invitrogen) to lift the cells from the culture dish. The cells were split at a 1:5 to a 1:20 ratio, depending on use. In between passages, the growth medium was changed every 2-3 days. One Merkel cell carcinoma stem cell culture has been passaged over 30 times without signs of senescence.

Example 6

Isolation and Culture of Prostate Carcinoma Stem Cells

Tissue from a prostate carcinoma was briefly rinsed in sterile phosphate buffered saline (PBS) containing 100 µg/mL gentamycin, placed in a 100 mm tissue culture dish, and minced into small (<1 mm) pieces. The minced tissue was suspended in 5 mL of dissociation media (F12/DMEM containing 100 µg/mL gentamycin and 200 µL collagenase-dispase (10% wt/vol in PBS) with soybean trypsin inhibitor (STI, 10%(v/v)) and incubated at 37° C. At 5-minute intervals, the suspension was pipetted to loosen cell aggregates. Enzymatic activity was stopped when aggregates of 10-20 cells appeared dissociated from the tissue.

The suspension was washed with F12/DMEM by centrifugation (4 minutes at 900 rpm) and the resulting cell pellet was resuspended in culture medium (serum free, calcium free F12/DMEM supplemented with calcium (0.1 mM), insulin (10 µg/mL), transferrin (10 µg/mL), EGF (5 ng/mL), selenium ($2.5 \times 10^{-8}$M), T3 ($1 \times 10^{-12}$M), ethanolamine ($1 \times 10^{-6}$M), phosphoethanolamine ($1 \times 10^{-6}$M), hydrocortisone ($1 \times 10^{-8}$M), testosterone (50 ng/mL), and PPE (about 15 µg total protein of PPE/mL)).

The cell suspension was transferred and divided into five laminin-coated 100 mm dishes. Culture medium was added for a final volume of 10 mL per dish and the dishes were incubated at standard incubation conditions.

The initial culture of the prostate carcinoma cells did not attach very well after three days in culture. When changing the media for these cells, the spent culture medium was collected and any attached cells were removed using collagenase-dispase. The spent culture medium and cells were centrifuged and the resulting cell pellet was resuspended in 10 ml of fresh growth media and plated into in a new laminin-coated culture dish. 10 ml of fresh growth media was also placed in the original dish plate and this dish (and subsequent used dishes) were carried with media changes every 2-3 days until an established culture of prostate carcinoma stem cells was generated. The average time for colonies of prostate carcinoma stem cells to appear in primary prostate cancer cultures was between 4-6 weeks.

FIG. 1A shows a small colony of prostate carcinoma stem cells growing out from the other cell types in culture after about 5 weeks in culture. The culture media was changed every 2-3 days but the cells were not passaged or split. As highlighted in the white circle, the prostate carcinoma stem cells can be distinguished from the other cells in culture by their morphology. They preferentially grew in tight colonies and had an epithelial cellular morphology. As compared to the other cells in culture, the prostate carcinoma stem cells were much smaller in size and therefore were further distinguished using this morphological feature.

After the establishment of small colonies, it is common that the prostate carcinoma stem cells will then enter exponential growth phase in the optimized growth media. FIG. 1B shows a small colony of prostate carcinoma stem cells starting exponential growth phase. FIG. 1C shows the same colony of prostate carcinoma stem cells after three days in exponential growth phase. FIG. 1D shows the same colony of prostate carcinoma stem cells after 6 days in exponential growth phase. Eventually, the prostate carcinoma stem cells formed an isolated, substantially pure population of cells and the other cell types were not present in the culture.

Once a substantially pure population of prostate carcinoma stem cells was established, the cells were passaged using standard techniques known in the art using collagenase-dispase to lift the cells off of the culture dish. Medium was changed every 3 days between passages. One prostate carcinoma stem cell line has been passaged over 30 times without signs of senescence.

Example 7

Isolation and Culture of Basal Cell Carcinoma Stem Cells

Tissue from a basal cell carcinoma was briefly rinsed in sterile phosphate buffered saline (PBS) containing 100 µg/mL gentamycin, placed in a 100 mm tissue culture dish, and minced into small (<1 mm) pieces. The minced tissue was suspended in 5 mL of dissociation media (F12/DMEM containing 100 µg/mL gentamycin and 200 µL collagenase-dispase (10% wt/vol in PBS) with soybean trypsin inhibitor (STI, 10% (v/v)) and incubated at 37° C. At 5-minute intervals, the suspension was pipetted to loosen cell aggregates. Enzymatic activity was stopped when aggregates of 10-20 cells appeared dissociated from the tissue.

The suspension was washed with F12/DMEM by centrifugation (4 minutes at 900 rpm) and the resulting cell pellet was resuspended in culture medium (serum free F12/DMEM supplemented with insulin (10 µg/mL), transferrin (10 µg/mL), EGF (5 ng/mL), selenium ($2.5 \times 10^{-8}$M), T3 ($1 \times 10^{-12}$M), ethanolamine ($1 \times 10^{-6}$M), phosphoethanolamine ($1 \times 10^{-6}$M), triiodothyronine (T3) ($1 \times 10^{-12}$M), hydrocortisone ($1 \times 10^{-8}$M), and PPE (about 75 µg total protein of PPE/mL)).

The cell suspension was transferred and divided into five fibronectin-coated 100 mm dishes. Culture medium was added for a final volume of 10 mL per dish and the dishes were incubated at standard incubation conditions. The medium is changed every 3 days until the stem cells with a small tightly packed morphology (see FIGS. 1-3) become apparent. At this point, as with the other cancer types, the stem cells begin to grow more rapidly. They can then be subcultured and after a few subcultures will be the only cell type remaining in the culture.

Once the basal cell carcinoma stem cell culture was about 85-95% confluent, the culture was sub-cultured using TrypLE Express (Invitrogen) to lift the cells from the culture dish. Alternatively, trypsin or collagenase-dispase can also be used. The cells were split at a 1:3 to a 1:5 ratio, depending on use. In between passages, the growth medium was changed every 3 days. One basal cell carcinoma stem cell culture has been passaged over 15 times without signs of senescence.

Example 8

Isolation and Culturing of Breast Carcinoma Stem Cells

Tissue from a breast carcinoma was briefly rinsed in sterile phosphate buffered saline (PBS) containing 100 µg/mL gentamycin, placed in a 100 mm tissue culture dish, and minced into small (<1 mm) pieces. The minced tissue was suspended in 5 mL of dissociation media (F12/DMEM containing 100 µg/mL gentamycin and 200 µL collagenase-dispase (10% wt/vol in PBS) with soybean trypsin inhibitor (STI, 10%(v/v)) and incubated at 37° C. At 5-minute intervals, the suspension was pipetted to loosen cell aggregates. Enzymatic activity was stopped when aggregates of 10-20 cells appeared dissociated from the tissue.

The suspension was washed with F12/DMEM by centrifugation (4 minutes at 900 rpm) and the resulting cell pellet was resuspended in culture medium (serum free F12/DMEM supplemented with insulin (10 µg/mL), transferrin (10 µg/mL), EGF (5 ng/mL), selenium ($2.5 \times 10^{-8}$M), T3 ($1 \times 10^{-12}$M), ethanolamine ($1 \times 10^{-6}$M), phosphoethanolamine ($1 \times 10^{-6}$M), hydrocortisone ($1 \times 10^{-8}$ M), prostaglandin E1 (PGE1) (100 ng/mL), and PPE (about 15 µg total protein of PPE/mL)).

The cell suspension was transferred and divided into five fibronectin-coated 100 mm dishes. Culture medium was added for a final volume of 10 mL per dish and the dishes were incubated at standard incubation conditions. Human breast carcinoma stem cells can be frozen using standard methods once the culture is established. When thawing the cells and putting them back in culture, a small about of fetal bovine serum (about 2% (v/v)) may be beneficial to ensure the survival of the human breast carcinoma stem cells. After the initial thaw and culture (e.g., 1-2 days), the culture medium with fetal bovine serum can be removed and replaced with serum-free medium. Fetal bovine serum is not required or preferred for the continued culture of the human breast carcinoma stem cells. Cultures conditions containing greater than 2% FBS have been shown to be inhibitory to the growth of human breast carcinoma stem cells.

Human breast carcinoma stem cells can be subcultured. The spent medium was aspirated off and 5 ml of DME/F12 medium was used to wash the cells. The wash medium was aspirated off and 1 ml of trypsin was added to the cells and the cells were incubated at 37° C. until the cells detached from the plate (approximately 5 minutes). One milliliter soybean trypsin inhibitor (STI) was added to neutralize the trypsin and the cells were collected and centrifuged to pellet. The cell pellet was resuspended in fresh growth medium and split at a ratio of 1:3 to 1:5 depending on use into fibronectin coated dishes. The growth medium was changed every 2-3 days and the cells were passaged or sub-cultured when they were 80-90% confluent. One breast carcinoma stem cell culture has been passaged over 25 times without signs of senescence.

Example 9

Characterization of Human Cancer Stem Cells

Experiments to characterize human cancer stem cells were performed, looking for cell surface expression of markers reported to be expressed on some cancer cells. CD24, CD34, CD44 and CD133 expression analyses of cells identified morphologically as cancer stem cells were performed using flow cytometry.

The cells were lifted from the flask using 2 ml of 0.2% Collagenase/dipase for 5 minutes or until cells dissociate or release from the flask. The cells were triturated using a 5 ml pipette to eliminate any cell clumps and then transferred to a 15 ml conical tube and spun down for 5 minutes at 1200 rpm. The supernatant was removed and the cells are resuspended in 1 ml/T75 flask or 5 ml/T175 flask of Analysis Buffer (Hank's Balanced Salt Solution with 1% BSA). Cells were counted using a hemacytometer.

50,000 to 100,000 cells were mixed with primary antibody and controls at the concentration listed below:
1. anti-CD24/PE at 100 µl/$10^8$ cells (Miltenyi)
2. anti-CD44/PE at 100 µl/$10^8$ cells (Miltenyi)
3. anti-CD34/PE at 10 µl/$10^5$ cells (Miltenyi)
4. anti-CD133/PE at 2 µl/$5 \times 10^4$ cells (Miltenyi)
5. Isotype control
6. FC Block at 100 µl/$10^8$ cells (Miltenyi)

The cells were then incubated in the dark at 4 degrees for 20 minutes.

After incubation, the volume was adjusted to 200 µl with Analysis Buffer and spun down for 5 seconds at 1200 rpm. The supernatant was removed and the cells were resuspended in 200 µl of fresh Analysis Buffer. 5 µl of 7-aminoactinomycin-D (7-AAD) or propidium iodide was added to the cells just prior to analysis for live/dead gating. The cells were analyzed using a FACSCalibur or Guava machine.

The results of the CD24, CD34, CD44 and CD133 expression on the cell lines are summarized in Table 1 and Table 2 below. In these tables "+" denotes a one log or higher shift in fluorescence intensity, "med" denotes a 0.5 to 1 log shift in fluorescence intensity, "low" denotes up to 0.5 log shift in fluorescence intensity and "–" denotes no shift in fluorescence intensity.

As shown in Table 1, a majority of the cancer stem cells expressed CD34, a known hematopoietic stem cell marker that has not previously been associated with solid cancer stem cells. Because CD34 is also known to be expressed on endothelial cells, as a control the expression of another endothelial cell marker (CD141) was examined. None of these cancer stem cells expressed CD141, thus, they are unlikely to be endothelial cells or hematopoietic cells.

To study the effects of metastasis on cancer stem cell markers, CD24, CD34 and CD44 expression analyses were performed on cancer stem cells that metastasized in animal xenograft experiments. Merkel cell carcinoma stem cells and 9926 (pancreatic carcinoma stem cells) were implanted in the sub-renal capsule of an immune-compromised mouse host. After about 6-8 weeks the animals were sacrificed and inspected for tumor formation. In addition to the primary tumor that formed on the kidney of the host, with both the Merkel and the 9926 cells, spontaneous metastases were observed in the body cavity of the host. These metastases were removed and cultured in the original growth medium. After the cells had grown up in culture, the cells were dispersed and analyzed for CD24, CD34, and CD44 expression using flow cytometry according to the methods described above. The results of these experiments are summarized below in Table 2.

With both Merkel and 9926 cell types, the parent cells showed a pattern of cellular surface marker expression that was different from the marker patterns on cells from metastatic deposits. The Merkel cell carcinoma lines derived from metastases showed high expression of CD44, low expression of CD24 and no expression of CD34. By comparison, the Merkel parent cells (that had not been animal passaged) had no expression of CD44, no expression of CD24 and high expression of CD34 (see Table 1). Similar results were also seen with the 9926 pancreatic carcinoma metastases, where the CD44 expression was high and CD34 expression was low, in comparison to the parent 9926 pancreatic carcinoma stem cells that had no CD44 expression and high CD34 expression.

To study the effects of animal passage on cancer stem cell markers, CD24, CD34 and CD44 expression analyses were also performed on cancer stem cells that were passaged through xenografts in an animal host. Three human cancer stem cell cultures (Merkel cell carcinoma, CRCA0404 and PRCA629a) were each placed in a mouse host as a xenograft (either in the subrenal capsule or subcutaneous), tumors were allowed to form, and then the primary tumors were removed and cultured in the appropriate medium for each cell type. After growing in culture, the cells were dispersed, and their level of CD24, CD34 and CD44 expression was analyzed using flow cytometry. The results are summarized below in Table 2.

Changes in the expression of cell surface markers were observed in the new primary tumors when compared to their parents. Cells from primary tumors from the Merkel cell carcinoma and also from the CRCA0404 colorectal carcinoma showed a loss of CD34 expression (as compared to the parental cancer stem cells) and a gain in CD44 expression. The cells from the PRCA629a tumor, which is very slow growing in vivo, retained high CD34 expression and had low CD44 expression. The results of these experiments suggest that passage through an animal may change the cell surface expression of markers that had been associated with their corresponding cancer stem cells.

In additional data not shown, changing cell culture conditions also may have an effect on cell surface markers; in the presence of forskolin, breast carcinoma cell line BRCA1103 shows a reduction in both CD44 and CD24 cell surface markers compared to their levels without forskolin.

TABLE 1

CD24, CD34, CD44 and CD133 expression in human cancer stem cell cultures

| Cell | CD34 | CD44 | CD24 | CD133 |
|---|---|---|---|---|
| CRCA0404 | + | Med | − | − |
| CRCA1115 | − | + | − | − |
| RECA0515 | − | + | − | − |
| RECA1208 | − | + | − | − |
| Lung carcinoma (CA130T308) | + | − | − | − |
| Pancreatic carcinoma (9926c5) | + | − | − | − |
| Merkel cell carcinoma | + | − | − | − |
| PRCA1004 | + | − | − | − |
| PRCA629a | + | − | − | ND |
| PRCA0312-58 | + | − | − | ND |
| PRCA0425-72 | + | − | − | ND |
| BRCA1103 | − | med | + | − |

TABLE 2

CD24, CD34 and CD44 expression on human cancer stem cells after animal passage (metastases and new primary tumors)

| Cell | CD34 | CD44 | CD24 |
|---|---|---|---|
| Merkel met | − | + | Low |
| 9926 met | low | + | − |

TABLE 2-continued

CD24, CD34 and CD44 expression on human cancer stem cells after animal passage (metastases and new primary tumors)

| Cell | CD34 | CD44 | CD24 |
|---|---|---|---|
| Merkel primary tumor | − | + | − |
| CRCA0404 primary tumor | − | + | − |
| PRCA629a primary tumor | + | low | − |

Example 10

Human Tumor Xenograft Model

Tumorigenic Potential of Human Cancer Stem Cells

Cancer stem cells are defined by being a small subset of tumor cells (initial selection by culture conditions) that are capable of self-renewal and that have the ability of forming tumors in vivo from a small number of cells. The tumor forming potential of the cancer stem cells were tested.

For these experiments, a range of cell number from 20 cells to $5 \times 10^4$ cells/collagen button were implanted into immune-deficient mice. The collagen button was prepared using type I rat-tail collagen. Preparation of type I rat-tail collagen is well known in the art. Briefly, tails from mature breeding rats were removed and the tendons were isolated and weighed. One gram of tendon produces 100 ml collagen solution, and each tail yields approximately 1 to 1.5 grams of tendon. To extract the collagen, the tendons were placed in a dilute acetic acid solution (200 µl glacial acetic per gram of tendon in 100 ml water) containing penicillin, streptomycin and fungizone and stirred gently at 4 degrees Celsius for at least one week. The solution was then centrifuged and the collagen supernatant was stored at 4 degrees Celsius until use.

For this study, 50 µl collagen buttons were prepared by polymerizing the rat-tail collagen in a setting solution containing Earle's Balanced Salt Solution (EBSS), NaOH and NaHCO$_3$. Following polymerization, varying cell numbers (from 20 to 200) were added per collagen button. The cells were incubated in collagen overnight at 37 degrees Celsius prior to implantation.

For implantation of the cells under the kidney capsule, mice were fully anesthetized with tribromoethanol. A pocket was made in the kidney capsule to allow for the placement of cells, which was made through a paralumbar surgical approach to the right and/or left kidney. Following surgery, the animals were allowed to recover on a heated surface and observed until fully recovered from the anesthesia. Wound clips were removed ten days post surgery. After 6-12 weeks in the animal, the kidneys of the animals were removed and visually inspected for tumor formation. Quantitative PCR (QPCR) was also performed on the kidneys using human Alu specific sequence primers to confirm and quantify tumor formation. The results are summarized in Table 3 below.

All of the cancer stem cells were capable of forming tumors in immune-deficient mice at innocula of about 200 cells. These tumors were usually visibly perceptible and were confirmed using QPCR. To date, all cancer stem cells tested can form tumors from innocula of 20 cells. (see Table 3). In all experiments, tumor formation was observed in 100% of the animals implanted with human cancer stem cells. Generally, at least three animals per condition were used in every experiment. These results are consistent with the characterization of these cells being cancer stem cells because of their ability to form tumors in vivo from a very small number of cells.

In contrast 2 cancer-derived cultures did not form tumors (see FIG. 4). If the dispersed prostate tumor cells were grown in serum (10%) containing medium for 2-4 weeks instead of selective medium, as described, the resulting culture would not for tumors when implanted at up to 250,000 cells/collagen button in the SRC. One of the colon cultures gave an anomalous cell line (CRCA0705) with a different morphology, growth characteristics, and cell surface protein binding characteristics. These cells will not form tumors at any inoculum of <200 to 500,000 cells/collagen button (see FIG. 4).

TABLE 3

Tumor formation in vivo using human cancer stem cells

| Cell type | # of cells inoculated | Site of inoculation | Time in vivo | Tumor formation? |
|---|---|---|---|---|
| Merkel cell carcinoma | ≦200 | Sub-renal capsule | 6 weeks | Yes |
|  | 20 |  | 7 weeks | Yes |
| Colorectal carcinoma | ≦200 | Sub-renal capsule | 6-8 weeks | Yes |
|  | 20 |  |  | Yes |
| Rectal carcinoma | ≦200 | Sub-renal capsule | 6-8 weeks | Yes |
|  | 20 |  |  | Yes |
| Lung carcinoma | ≦200 | Sub-renal capsule | 8 weeks | Yes |
|  | 20 |  | 7 weeks | Yes |
| Prostate carcinoma | ≦200 | Sub-renal capsule | 8 weeks | Yes |
|  | 20 |  | 7 weeks | Yes |
| Breast carcinoma | ≦200 | Sub-renal capsule | 6-8 weeks | Yes |
| Pancreatic carcinoma | ≦200 | Sub-renal capsule | 6-8 weeks | Yes |

FIG. 4 shows photos of tumors formed under the kidney capsule of SCID mice from various cell lines. As shown in that figure, the cancer stem cell lines are clearly distinguishable from the non-cancer stem cell lines using this subrenal cancer xenograft model.

Example 11

Human Tumor Xenograft Model

Metastatic Potential of Human Cancer Stem Cells

This study was designed to use Merkel cell carcinoma stem cells cultured from a Merkel cell carcinoma (neuroendocrine cancer of the skin) in a human tumor xenograft model. The MCC cells when implanted in the subrenal capsule will form a tumor that will spontaneously metastasize to multiple organs in the peritoneal and chest cavities. The metastases can be seen visually, or quantified using the QPCR for human DNA.

Type I rat-tail collagen was prepared by the method described above. For this study, 50 μl collagen buttons were prepared by polymerizing the rat-tail collagen in a setting solution containing Earle's Balanced Salt Solution (EBSS), NaOH and $NaHCO_3$. Following polymerization, $5 \times 10^5$ Merkel cells were added per collagen button. The cells were incubated in collagen overnight at 37° C. prior to implantation.

For implantation of the cells under the kidney capsule, mice were fully anesthetized with tribromoethanol. A pocket was made in the kidney capsule to allow for the placement of cells, which was made through a paralumbar surgical approach to the right and/or left kidney. In some studies, both kidneys received xenografts. Following surgery, the animals were allowed to recover on a heated surface and observed until fully recovered from the anesthesia. Wound clips were removed ten days post-surgery.

The tumors were allowed to grow for approximately 5-8 weeks. At the end of the study, the mice were sacrificed and the tumors removed. A significant number of metastases were found in the mice. Metastases could be found in the omentum, diaphragm, spleen, ovary and lungs of the mice with the implanted Merkel cell carcinoma cell cultures. Generally, the metastases were large in size and were easily perceptible to the naked eye.

Similar experiments were performed using RECA0515 cells and CRCA1115 cells. Both cell types will metastasize to multiple sites from the sub-renal capsule. Experiments using the 9926 pancreatic cancer stem cells resulted in metastasis from the sub-renal capsule to other sites in the mouse. Also, 9926 pancreatic cancer stem cells metastasized at a greater frequency when implanted in the mouse prostate as compared to implantation under the renal capsule. Take together as a whole, these results show that human cancer stem cell cultures can be used in a successful xenograft model to understand the establishment, growth and metastasis of human tumors in vivo.

Interestingly, in similar experiments, 4 of the PRCA lines will also metastasize spontaneously from the SRC after 4 to 12 weeks in the animal, even when (in some cases) a very few (<500) cells were implanted.

It has been predicted that cancer stem cells are the cell type in the tumor that metastasizes to distant sites [see Li, F. Tiede, B., Massague, J. & Kang, Y. (2007) *Cell Res* 17, 3-14]. With this in mind it is interesting to note that four of the prostate CSC described herein will spontaneously metastasize to multiple organs from tumors grown from cells implanted in the SRC. In addition, the CRCA1115 colon tumor-derived line, the Merkel-derived line, and the CTLY (cutaneous T cell lymphoma-derived line) all metastasize from SRC tumors. The PACA pancreatic derived line will metastasize from tumors orthotopically implanted in the pancreas. Thus these CSC lines frequently exhibit the property of spontaneous metastasis from a primary solid tumor xenograft, a characteristic rarely seen in ATCC tumor derived cell lines and most other lines. A partial list of tumor-derived cell lines, with their tissue and cell line phenotype, obtained according to the teachings of this invention, are shown in Table 4.

TABLE 4

Tumor derived cell lines

| Cell Line Designation | Tissue & cell line phenotype | | Passage # | In-vivo growth & metastasis |
|---|---|---|---|---|
| PRCA629* | Prostate | Stem cell-like | >20 | √ |
| PRCA1004* | Prostate | Stem cell-like | >30 | √ |
| PRCA0312-58* | Prostate | Stem cell-like | 20 | √ |
| PRCA0312-43e* | Prostate | Stem cell-like | 6 | √ metastatic |

TABLE 4-continued

Tumor derived cell lines

| Cell Line Designation | Tissue & cell line phenotype | | Passage # | In-vivo growth & metastasis |
|---|---|---|---|---|
| PRCA0425* | Prostate | Stem cell-like | 17 | √ metastatic |
| PRCA0611* | Prostate | Stem cell-like | 10 | √ |
| PRCA 0806 | Prostate | Stem cell-like | 3 | √ metastatic |
| PRCA0702 | Prostate | Stem cell-like | 7 | √ metastatic |
| PRCA0312-43STR* | Prostate | Stromal-mixed culture | 2 | NO |
| CRCA0404* | RA Colon | Stem cell-like | 22 | √ |
| CRCA1115* | Colon | Stem cell-like | >30 | √ metastatic |
| RECA0515* | Rectal | Stem cell-like | 21 | √ |
| RECA1208* | Rectal | Stem cell-like | 9 | √ |
| RECA0705* | Rectal | | 5 | NO |
| PA9926* | Pancreatic ductal | Stem cell-like | >50 | √ metastatic |
| CA130* | Lung adenocarcinoma | Stem cell-like | >50 | √ |
| LUCA9979 | Lung adenocarcinoma | Stem cell-like | >20 | √ |
| MCLY* | Mantle cell lymphoma | lymphoma | >20 | √ |
| CTLY | Cutaneous T cell | lymphoma | 4 | √ metastatic |
| BRCA1103 | Breast ductal carcinoma | Stem cell-like | >30 | √ |
| BCC | Basal cell carcinoma | Stem cell-like | 4 | |
| BCC2 | Basal cell carcinoma | Stem cell-like | 4 | |
| BCCA0517 | Basal cell carcinoma | Stem cell-like | 2 | |
| Aβcc/MEL | Melanoma | Stem cell-like | 12 | |
| MCC* (MRKL) | Merkel cell | Stem cell-like | >30 | √ metastatic |

*data shown using these cell lines

Experiments were also performed to determine the effects of antibodies on the growth of cancer cell metastases. As shown in FIGS. 5 and 6, the antibody KID24 (PTA-5174), known to bind to the surface of certain cancers, decreased the growth of tumor metastases from cancer stem cell line cancers established in subrenal capsule models.

It is understood that the examples and embodiments described herein are for illustrative purposes only and that various modifications or changes in light thereof will be suggested to persons skilled in the art and are to be included within the spirit and purview of this application. All publications, patents and patent applications cited herein are hereby incorporated by reference in their entirety for all purposes to the same extent as if each individual publication, patent or patent application were specifically and individually indicated to be so incorporated by reference.

The invention claimed is:

1. A population of human solid cancer stem cells, wherein said cancer stem cells have been isolated from human solid tumor tissue, and grown in a nutrient media optimized for their growth, and wherein said population of human solid cancer stem cells is sufficiently free of other cell types such that an inoculum of about 200 of said cancer stem cells is capable of forming tumors within eight weeks in an immune-deficient mouse, and said cancer stem cells are:
  a) colorectal carcinoma stem cells that express cell surface marker CD34 and not CD24;
  b) lung carcinoma stem cells that express cell surface marker CD34 and not CD24.
  c) pancreatic carcinoma stem cells that express cell surface marker CD34 and not CD24;
  d) rectal carcinoma stem cells that express CD44 and not CD24;
  e) Merkel cell carcinoma stem cells that express CD34 and not CD24;
  f) prostate carcinoma stem cells that express CD34 and not CD24; or
  g) breast carcinoma stem cells that express CD24 and not CD34.

2. The population of human cancer stem cells of claim 1, wherein said cells retain the capacity for extensive sub-culturing without senescence.

3. The population of human cancer stem cells of claim 1, wherein said cells are colorectal carcinoma stem cells, rectal carcinoma stem cells or prostate carcinoma stem cells.

4. The population of human cancer stem cells of claim 1, wherein said cells are lung carcinoma stem cells.

5. The population of human cancer stem cells of claim 1, wherein said cells are pancreatic carcinoma stem cells.

6. The population of human cancer stem cells of claim 1, wherein said cells are Merkel cell carcinoma stem cells.

7. The population of human cancer stem cells of claim 1, wherein said cells are breast carcinoma stem cells.

8. The population of human solid cancer stem cells of claim 1, wherein said cancer stem cells have been subcultured to obtain said population of said human solid cancer stem cells.

9. A method of isolating a population of human solid cancer stem cells comprising:
  (A) dissociating a source of human cancer stem cells from a corresponding tissue type of solid human tumor;
  (B) placing said dissociated source of human cancer stem cells in a nutrient media that has been optimized for the growth of human cancer stem cells;
  (C) maintaining suitable culture conditions sufficient to support the growth of human cancer stem cells in said nutrient media; and
  (D) subculturing said population of human cancer stem cells to obtain a population of said human solid cancer stem cells, and wherein said population of said human solid cancer stem cells is sufficiently free of other cells such that an inoculum of about 200 of said cancer stem cells is capable of forming tumors within eight weeks in an immune-deficient mouse, and said cancer stem cells are:
   1) colorectal carcinoma stem cells that express cell surface marker CD34 and not CD24;
   2) lung carcinoma stem cells that express cell surface marker CD34 and not CD24;

3) pancreatic carcinoma stem cells that express cell surface marker CD34 and not CD24;
4) rectal carcinoma stem cells that express CD44 and not CD24;
5) Merkel cell carcinoma stem cells that express CD34 and not CD24;
6) prostate carcinoma stem cells that express CD34 and not CD24; or
7) breast carcinoma stem cells that express CD24 and not CD34.

10. The method of claim 9, wherein said cells are colorectal carcinoma stem cells, rectal carcinoma stem cells or prostate carcinoma stem cells.

11. The method of claim 9, wherein said cells are lung carcinoma stem cells, pancreatic carcinoma stem cells, or Merkel cell carcinoma stem cells.

12. The method of claim 9, wherein said cells are breast carcinoma stem cells.

* * * * *